(12) United States Patent
Morris et al.

(10) Patent No.: US 10,688,246 B2
(45) Date of Patent: Jun. 23, 2020

(54) SPACE SAVING DRUG INJECTION DEVICE

(71) Applicant: Sanofi, Paris (FR)

(72) Inventors: Anthony Paul Morris, West Midlands (GB); Matthew Meredith Jones, Warwick (GB); Oliver Benjamin Brown, Stroud (GB)

(73) Assignee: Sanofi, Paris (FR)

( * ) Notice: Subject to any disclaimer, the term of this patent is extended or adjusted under 35 U.S.C. 154(b) by 337 days.

(21) Appl. No.: 15/533,909

(22) PCT Filed: Dec. 9, 2015

(86) PCT No.: PCT/EP2015/079141
§ 371 (c)(1),
(2) Date: Jun. 7, 2017

(87) PCT Pub. No.: WO2016/091960
PCT Pub. Date: Jun. 16, 2016

(65) Prior Publication Data
US 2017/0319788 A1 Nov. 9, 2017

(30) Foreign Application Priority Data
Dec. 10, 2014 (EP) .................................. 14306995

(51) Int. Cl.
*A61M 5/315* (2006.01)
*A61M 5/20* (2006.01)
(Continued)

(52) U.S. Cl.
CPC .......... *A61M 5/31511* (2013.01); *A61M 5/20* (2013.01); *A61M 5/2033* (2013.01);
(Continued)

(58) Field of Classification Search
CPC .......... A61M 5/31541; A61M 5/31551; A61M 5/31553; A61M 5/31533; A61M 5/3155; A61M 5/31528; A61M 5/31555
See application file for complete search history.

(56) References Cited

U.S. PATENT DOCUMENTS

2007/0060894 A1* 3/2007 Dai .................. A61M 5/19
604/207
2007/0276329 A1 11/2007 Mernoe
(Continued)

FOREIGN PATENT DOCUMENTS

| WO | WO 02/076531 | 10/2002 |
|---|---|---|
| WO | WO 2011/136718 | 11/2011 |

(Continued)

OTHER PUBLICATIONS

International Preliminary Report on Patentability in International Application No. PCT/EP2015/079141, dated Jun. 13, 2017, 10 pages.
(Continued)

Primary Examiner — Emily L Schmidt
(74) Attorney, Agent, or Firm — Fish & Richardson P.C.

(57) ABSTRACT

The present disclosure relates to an injection device for setting and dispensing of a dose of a medicament, the device including an elongated housing to accommodate a cartridge filled with the medicament and sealed with a piston, a piston rod extending along a first axis and being threadedly or slidingly engaged with the housing to apply a distally directed thrust to the piston of the cartridge, a drive member rotationally or threadedly engaged with the piston rod and having a wheel section or geared section, and a drive sleeve extending along a second axis at a radial distance from the first axis and having a geared section to mesh with the wheel section or geared section of the drive member, wherein a first radial distance between first and second axes at a distal end
(Continued)

of the drive sleeve differs from a second radial distance between first and second axes at a proximal end of the drive sleeve.

18 Claims, 8 Drawing Sheets

Specification includes a Sequence Listing.

(51) Int. Cl.
  *A61M 5/24* (2006.01)
  *A61M 5/31* (2006.01)
(52) U.S. Cl.
  CPC ............ *A61M 5/24* (2013.01); *A61M 5/3157* (2013.01); *A61M 5/31536* (2013.01); *A61M 5/31541* (2013.01); *A61M 5/31575* (2013.01); *A61M 5/31578* (2013.01); *A61M 5/31583* (2013.01); *A61M 5/31593* (2013.01); *A61M 5/31535* (2013.01); *A61M 2005/3126* (2013.01); *A61M 2005/3154* (2013.01); *A61M 2005/31518* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 2015/0126926 A1* | 5/2015 | Giambattista | A61M 5/1454 604/135 |
| 2016/0114109 A1* | 4/2016 | Lavi | A61M 5/1452 604/82 |
| 2016/0220759 A1* | 8/2016 | Enggaard | A61M 5/31541 |
| 2016/0271335 A1* | 9/2016 | Higson | A61M 5/31583 |

FOREIGN PATENT DOCUMENTS

| | | |
|---|---|---|
| WO | WO 2012/038721 | 3/2012 |
| WO | WO 2013/153041 | 10/2013 |
| WO | WO 2013/156224 | 10/2013 |
| WO | WO 2014/166888 | 10/2014 |
| WO | WO 2014/166917 | 10/2014 |
| WO | WO 2014/166926 | 10/2014 |

OTHER PUBLICATIONS

International Search Report and Written Opinion in International Application No. PCT/EP2015/079141, dated Feb. 5, 2016, 12 pages.

\* cited by examiner

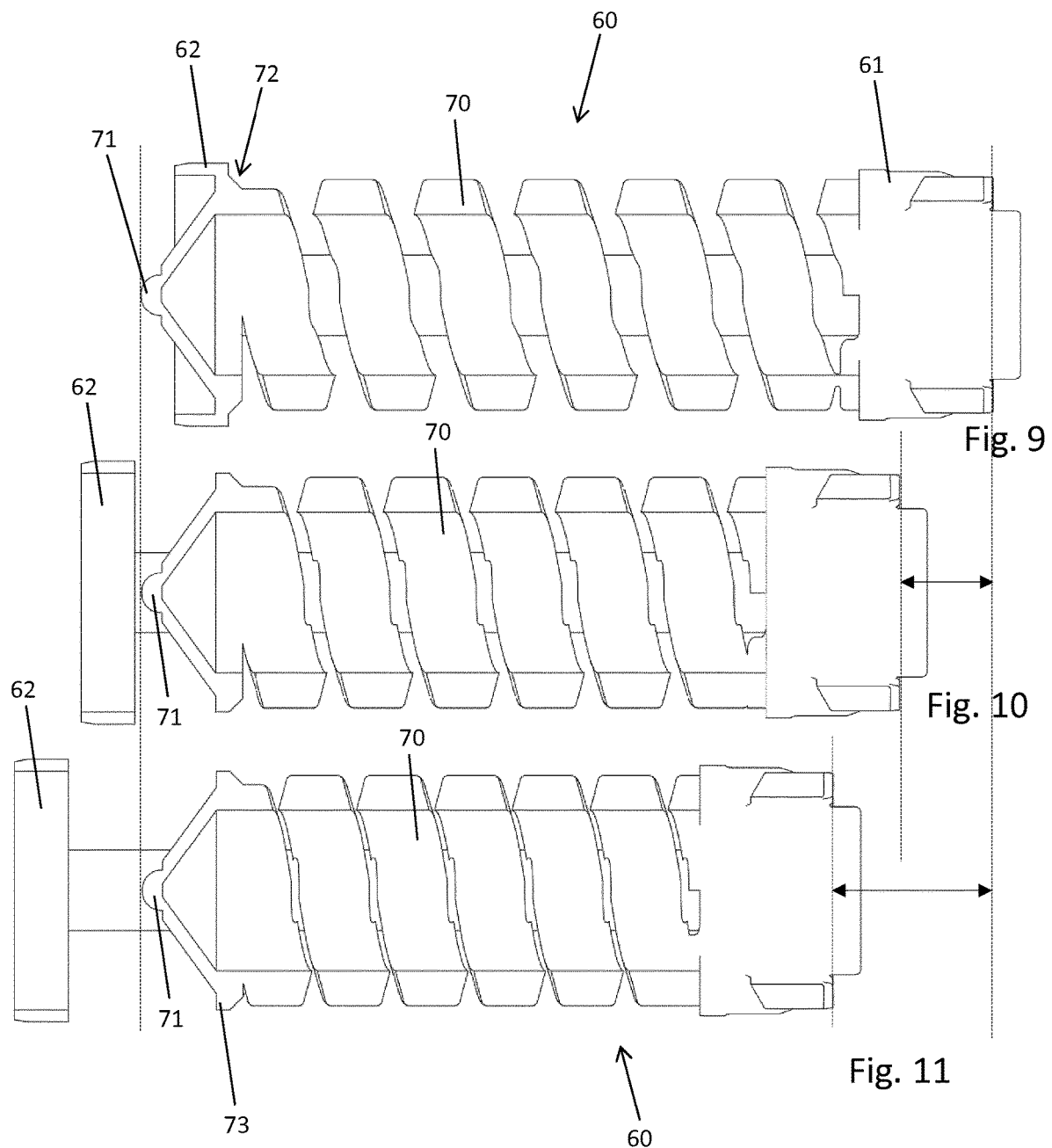

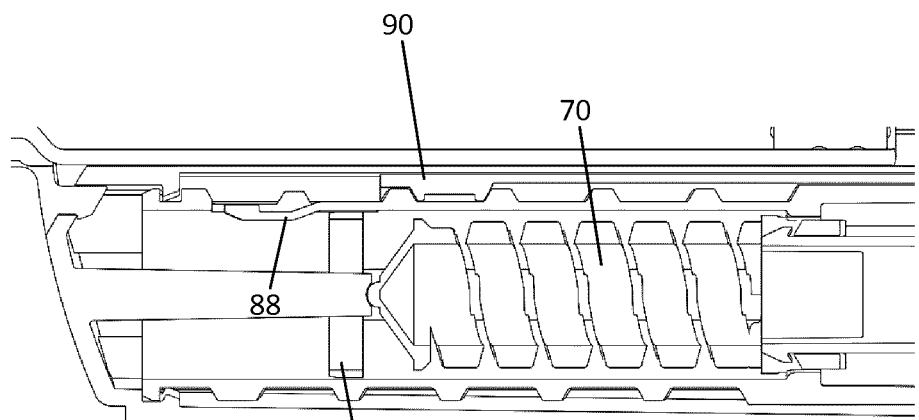
Fig. 16
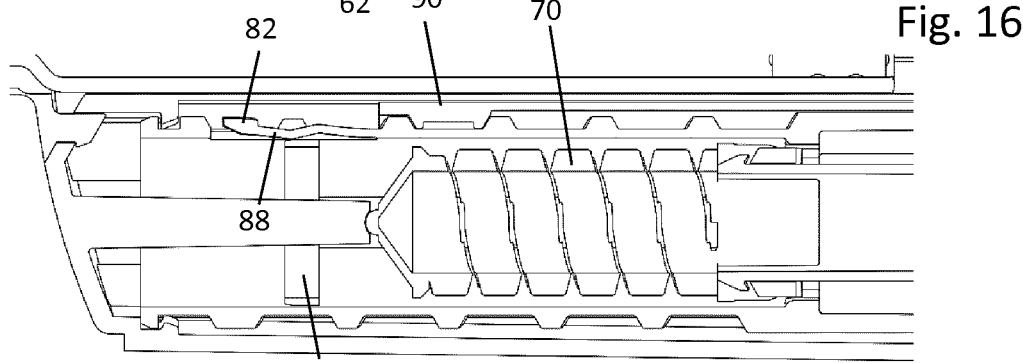
Fig. 17
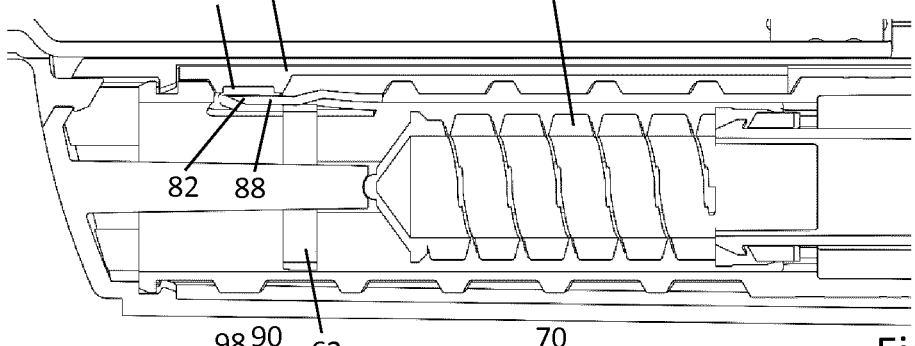
Fig. 18
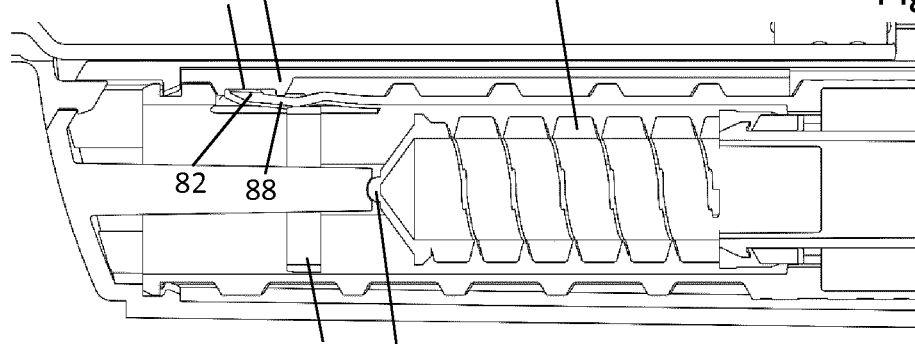
Fig. 19
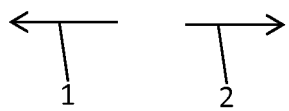

SEQUENCE LISTING

<160> NUMBER OF SEQ ID NOS: 40

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 2
<211> LENGTH: 41
<212> TYPE: PRT
<213> ORGANISM: Artificial Sequence
<220> FEATURE:
<223> OTHER INFORMATION: H-(Lys)4-des Pro36, des Pro37 Exendin-4(1-39)-NH2

<400> SEQUENCE: 2

```
Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40
```

<210> SEQ ID NO 3
<211> LENGTH: 42
<212> TYPE: PRT
<213> ORGANISM: Artificial Sequence
<220> FEATURE:
<223> OTHER INFORMATION: H-(Lys)5-des Pro36, des Pro37 Exendin-4(1-39)-NH2

<400> SEQUENCE: 3

```
Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30

Asn Gly Gly Pro Ser Ser Gly Ala Pro Ser
        35                  40
```

<210> SEQ ID NO 4
<211> LENGTH: 38
<212> TYPE: PRT
<213> ORGANISM: Artificial Sequence
<220> FEATURE:
<223> OTHER INFORMATION: des Pro36 Exendin-4(1-39)

<400> SEQUENCE: 4

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```

<210> SEQ ID NO 5
<211> LENGTH: 38
<212> TYPE: PRT
<213> ORGANISM: Artificial Sequence
<220> FEATURE:
<223> OTHER INFORMATION: des Pro36 [Asp28] Exendin-4(1-39)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: des Pro36 [IsoAsp28] Exendin-4(1-39)
<220> FEATURE:
<221> NAME/KEY: MISC_FEATURE
<222> LOCATION: (28)..(28)
<223> OTHER INFORMATION: x=isoaspartate

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 7
<211> LENGTH: 38
<212> TYPE: PRT
<213> ORGANISM: Artificial Sequence
<220> FEATURE:
<223> OTHER INFORMATION: des Pro36 [Met(O)14, Asp28] Exendin-4(1-39)
<220> FEATURE:
<221> NAME/KEY: MISC_FEATURE
<222> LOCATION: (14)..(14)
<223> OTHER INFORMATION: x=methionine oxide

<400> SEQUENCE: 7

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 8
<211> LENGTH: 38
<212> TYPE: PRT
<213> ORGANISM: Artificial Sequence
<220> FEATURE:
<223> OTHER INFORMATION: des Pro36 [Met(O)14, IsoAsp28] Exendin-4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (28)..(28)
<223> OTHER INFORMATION: x=isoaspartate

<400> SEQUENCE: 8

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 9
<211> LENGTH: 38
<212> TYPE: PRT
<213> ORGANISM: Artificial Sequence
<220> FEATURE:
<223> OTHER INFORMATION: des Pro36 [Trp(O2)25, Asp28] Exendin-4(1-39)
<220> FEATURE:
<221> NAME/KEY: MISC_FEATURE
<222> LOCATION: (25)..(25)
<223> OTHER INFORMATION: x=tryptophan dioxide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
<223> OTHER INFORMATION: des Pro36 [Trp(O2)25, IsoAsp28] Exendin-4(1-39)
<220> FEATURE:
<221> NAME/KEY: MISC_FEATURE
<222> LOCATION: (25)..(25)
<223> OTHER INFORMATION: x=tryptophan dioxide
<220> FEATURE:
<221> NAME/KEY: MISC_FEATURE
<222> LOCATION: (28)..(28)
<223> OTHER INFORMATION: x=isoaspartate

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 11
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, Asp28] Exendin-
      4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)

<223> OTHER INFORMATION: x=tryptophan dioxide

<400> SEQUENCE: 11

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, IsoAsp28]
      Exendin-4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan dioxide
<220> FEATURE:
<221> NAME/KEY: MISC_FEATURE
<222> LOCATION: (28)..(28)
<223> OTHER INFORMATION: x=isoapartate

<400> SEQUENCE: 12

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 13
<211> LENGTH: 44
<212> TYPE: PRT
<213> ORGANISM: Artificial Sequence
<220> FEATURE:
<223> OTHER INFORMATION: des Pro36 Exendin-4(1-39)-Lys6-NH2

<400> SEQUENCE: 13

His Gly Glu Gly Thr Lys Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 14
<211> LENGTH: 50
<212> TYPE: PRT
<213> ORGANISM: Artificial Sequence
<220> FEATURE:
<223> OTHER INFORMATION: H-(Lys)6-des Pro36 [Asp28] Exendin-4(1-39)-
      Lys6-NH2

<400> SEQUENCE: 14

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu

Lys Asp Gly Gly Pro Ser Ser Gly Ala Pro Pro Ser Lys Lys Lys Lys
            35                  40                  45

Lys Lys
    50

<210> SEQ ID NO 15
<211> LENGTH: 38
<212> TYPE: PRT
<213> ORGANISM: Artificial Sequence
<220> FEATURE:
<223> OTHER INFORMATION: des Asp28 Pro36, Pro37, Pro38Exendin-4(1-39)-
      NH2

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Pro Ser
        35

<210> SEQ ID NO 16
<211> LENGTH: 44
<212> TYPE: PRT
<213> ORGANISM: Artificial Sequence
<220> FEATURE:
<223> OTHER INFORMATION: H-(Lys)6-des Pro36, Pro38 [Asp28] Exendin-4(1-
      39)-NH2

<400> SEQUENCE: 16

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 17
<211> LENGTH: 44
<212> TYPE: PRT
<213> ORGANISM: Artificial Sequence
<220> FEATURE:
<223> OTHER INFORMATION: H-Asn-(Glu)5des Pro36, Pro37, Pro38 [Asp28]
      Exendin-4(1-39)-NH2

<400> SEQUENCE: 17

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 18
<211> LENGTH: 44
<212> TYPE: PRT
<213> ORGANISM: Artificial Sequence
<220> FEATURE:
<223> OTHER INFORMATION: des Pro36, Pro37, Pro38 [Asp28] Exendin-4(1-
      39)-(Lys)6-NH2

<400> SEQUENCE: 18

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40
```

<210> SEQ ID NO 19
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Asp28]
     Exendin-4(1-39)-(Lys)6-NH2

<400> SEQUENCE: 19

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50
```

<210> SEQ ID NO 20
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Asp28]
     Exendin-4(1-39)-(Lys)6-NH2

<400> SEQUENCE: 20

```
Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50
```

<210> SEQ ID NO 21
<211> LENGTH: 50
<212> TYPE: PRT
<213> ORGANISM: Artificial Sequence
<220> FEATURE:
<223> OTHER INFORMATION: H-(Lys)6-des Pro36 [Trp(O2)25, Asp28] Exendin-
     4(1-39)-Lys6-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 21

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45
```

Lys Lys
    50

<210> SEQ ID NO 22
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Trp(O2)25]
      Exendin-4(1-39)-NH2
<220> FEATURE:
<221> NAME/KEY: MISC_FEATURE
<222> LOCATION: (25)..(25)
<223> OTHER INFORMATION: x=tryptophan dioxide

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 23
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 23

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 24
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 24

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 25
<211> LENGTH: 44
<212> TYPE: PRT

```
<213> ORGANISM: Artificial Sequence
<220> FEATURE:
<223> OTHER INFORMATION: des Pro36, Pro37, Pro38 [Trp(O2)25, Asp28]
      Exendin-4(1-39)-(Lys)6-NH2
<220> FEATURE:
<221> NAME/KEY: MISC_FEATURE
<222> LOCATION: (25)..(25)
<223> OTHER INFORMATION: x=tryptophan dioxide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 26
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-(Lys)6-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 26

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 27
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-(Lys)6-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 27

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 28
<211> LENGTH: 50
<212> TYPE: PRT
<213> ORGANISM: Artificial Sequence
```

```
<220> FEATURE:
<223> OTHER INFORMATION: H-(Lys)6-des Pro36 [Met(O)14, Asp28] Exendin-
      4(1-39)-Lys6-NH2
<220> FEATURE:
<221> NAME/KEY: MISC_FEATURE
<222> LOCATION: (20)..(20)
<223> OTHER INFORMATION: x=methionine oxide

<400> SEQUENCE: 28

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 29
<211> LENGTH: 38
<212> TYPE: PRT
<213> ORGANISM: Artificial Sequence
<220> FEATURE:
<223> OTHER INFORMATION: des Met(O)14 Asp28 Pro36, Pro37, Pro38 Exendin-
      4(1-39)-NH2

<400> SEQUENCE: 29

His Gly Glu Gly Thr Phe Thr Ser Asp Leu Ser Lys Gln Glu Glu Glu
1               5                   10                  15

Ala Val Arg Leu Phe Ile Glu Trp Leu Lys Asp Gly Gly Pro Ser Ser
            20                  25                  30

Gly Ala Pro Pro Pro Ser
        35

<210> SEQ ID NO 30
<211> LENGTH: 44
<212> TYPE: PRT
<213> ORGANISM: Artificial Sequence
<220> FEATURE:
<223> OTHER INFORMATION: H-(Lys)6-desPro36, Pro37, Pro38 [Met(O)14,
      Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide

<400> SEQUENCE: 30

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 31
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide
```

```
<400> SEQUENCE: 31

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 32
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Asp28]
      Exendin-4(1-39)-(Lys)6-NH2
<220> FEATURE:
<221> NAME/KEY: MISC_FEATURE
<222> LOCATION: (14)..(14)
<223> OTHER INFORMATION: x=methionine oxide

<400> SEQUENCE: 32

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 33
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide

<400> SEQUENCE: 33

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 34
<211> LENGTH: 50
<212> TYPE: PRT
<213> ORGANISM: Artificial Sequence
<220> FEATURE:
<223> OTHER INFORMATION: H-Asn-(Glu)5 des Pro36, Pro37, Pro38 [Met(O)14,
      Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide

<400> SEQUENCE: 34

Asn Glu Glu Glu Glu Glu His Gly Glu Gly Thr Phe Thr Ser Asp Leu
1               5                   10                  15
```

```
Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 35
<211> LENGTH: 50
<212> TYPE: PRT
<213> ORGANISM: Artificial Sequence
<220> FEATURE:
<223> OTHER INFORMATION: H-Lys6-des Pro36 [Met(O)14, Trp(O2)25, Asp28]
      Exendin-4(1-39)-Lys6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan dioxide

<400> SEQUENCE: 35

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 36
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Met(O)14,
      Trp(O2)25] Exendin-4(1-39)-NH2
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan oxide

<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Gly Gly Pro Ser Ser
            20                  25                  30

Gly Ala Pro Pro Ser
        35

<210> SEQ ID NO 37
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-NH2
<220> FEATURE:
<221> NAME/KEY: MISC_FEATURE
```

```
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 37

Asn Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 38
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Trp(O2)25,
      Asp28] Exendin-4(1-39)-(Lys)6-NH2
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan oxide

<400> SEQUENCE: 38

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 39
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Trp(O2)25, Asp28] Exendin-4(S1-39)-(Lys)6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 39

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 40
```

```
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 40

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50
```

SPACE SAVING DRUG INJECTION DEVICE

CROSS-REFERENCE TO RELATED APPLICATIONS

This application is a U.S. national stage application under 35 USC § 371 of International Application No. PCT/EP2015/079141, filed on Dec. 9, 2015, which claims priority to European Patent Application No. 14306995.3, filed on Dec. 10, 2014, the entire contents of which are incorporated herein by reference.

DESCRIPTION

The present disclosure relates to a drive mechanism of a drug delivery device and to a drive mechanism of an injection device, such like an injection pen. In particular the disclosure relates to a drive mechanism of a disposable injection device that allows and enables a user of the device to select or to set a dose of a medicament of variable size and to dispense or to inject the dose.

SEQUENCE LISTING

The instant application contains a Sequence Listing which has been submitted electronically in ASCII format and is hereby incorporated by reference in its entirety. Said ASCII copy, created on Mar. 17, 2020, is named "Sequence Listing" and is 28 KB in size.

BACKGROUND AND PRIOR ART

Injection devices for setting and dispensing a single dose or multiple doses of a liquid medicament are as such well-known in the art. Generally, such devices have substantially a similar purpose to that of an ordinary syringe.

Injection devices, in particular pen-type injectors have to meet a number of user-specific requirements. For instance, with patients suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous tubular shaped barrel sealed in distal direction by means of a pierceable seal and being further sealed in the proximal direction by the piston. With reusable injection devices an empty cartridge is replaceable by a new one. In contrast to that, injection devices of disposable type are to be entirely discarded when the medicament in the cartridge has been dispensed or used-up.

Many injection devices, of e.g. pen-injector type, provide multiple and frequent dispensing and injection of the liquid medicament. For this, the piston rod of the drive mechanisms of such devices advances in discrete steps in a distal direction during repeated dose dispensing procedures until an end-of-content configuration has been reached, in which the piston of the cartridge reaches a distal stop or end configuration. In order to provide a safe and convenient handling of such devices it is a general aim, that the device provides audible, visual as well as tactile feedback during dose setting as well as during dose dispensing procedures. Moreover, with non-electrical and purely mechanically implemented injection devices it is a further aim that the device itself provides or generates a driving force or driving torque during dose dispensing so that the user is no longer obliged to exert a particular driving force for dose dispensing. This is generally achievable by making use of mechanical energy storing means, e.g. implemented as a spring element, which has to be arranged inside the device in a rather space saving way.

It is a general aim for both, reusable as well as for disposable injection devices, to limit the total number of parts and to optimize the space inside the device in order to provide a rather compact and cost-attractive design. From WO 2013/156224 A1 an injection device for setting and injecting set doses from drug cartridge is known. There, a drive nut and a drive member are arranged at a radial distance. They are arranged along two longitudinally and parallel extending axes that are spaced from each other in radial direction. The radial separation of mutually engaging components of a drive mechanism of such an injection device is governed for instance by the size, in particular by the diameter of a tubular cartridge, by the diameter of sleeve-shaped elements, such like a dose indicating sleeve and the geometric package of mutually engaging components of the drive mechanism that might be engaged in a manifold of different ways.

SUMMARY

The present disclosure provides a space optimized injection device for setting and for dispensing of a dose of a medicament. The injection device can reduce the overall number of movable components of the injection device. The present disclosure further provides a rather simple and user-friendly handling of the injection device and of its drive mechanism. The injection device can further provide a visual, tactile and audible feedback during both dose setting and dose dispensing.

In a first aspect an injection device for setting and dispensing of at least a single, typically of multiple doses of a medicament, especially of a liquid medicament includes an elongated housing to accommodate a cartridge filled with the medicament. The cartridge is typically sealed with a piston or bung towards its proximal direction. The elongated housing defines an axial direction that coincides with the distal and with the proximal direction. The housing therefore comprises a distal end facing towards biological tissue and further comprises an oppositely located proximal end facing away from biological tissue, into which the medicament is to be injected.

The injection device comprises a drive mechanism comprising numerous mechanically interacting or inter-engaging components that are rotatable and/or axially displaceable relative to each other as well as relative to the housing in order to set a dose of variable size and for subsequently dispensing the set dose of the medicament. The injection device comprises a piston rod extending along a first axis and being radially or slidingly engaged with the housing to apply a distally directed thrust to the piston of the cartridge. The piston rod is adapted to advance in distal direction so as to exert distally directed pressure to the piston of the cartridge. In this way, a fluid pressure inside the cartridge can be increased to expel a predefined amount of the medicament from the cartridge. For the purpose of injecting the medicament into biological tissue the cartridge is typically connected with a piercing assembly having a double-tipped injection needle, which needle being in fluid communication with the interior of the cartridge.

Due to its threaded or sliding engagement with the housing the piston rod is displaceable in the distal direction relative to the housing. In a sliding engagement the piston rod is keyed or splined to a correspondingly-shaped structure to the housing. In this context, a sliding, splined or a keyed engagement rather means that the piston rod is rotatably locked to the housing but is free to slide in an axial direction relative to the housing. This is typically obtained by at least one radial protrusion of the housing or piston rod engaging with a correspondingly shaped radial groove of the piston rod or the housing.

The injection device further comprises a drive member rotatably or threadedly engaged with the piston rod. When rotationally engaged with the piston rod, drive member and piston rod are typically splined or keyed so that the drive member being axially fixed to the housing, is rotatable in order to induce a corresponding rotation of the piston rod. In this embodiment the piston rod is typically threadedly engaged with the housing so that a rotation of the piston rod induced by a rotation of the drive member leads to a distally directed displacement of the piston rod relative to the housing and relative to a barrel of the cartridge, thereby displacing the piston of the cartridge relative to the barrel for expelling a predefined amount of the medicament from the cartridge.

According to an alternative embodiment the drive member is threadedly engaged with the piston rod so that the piston rod experiences a distally directed displacement relative to the housing while being splined or keyed to the housing.

The drive member further comprises a wheel section, typically at its outer circumference. The wheel section may have the shape of a geared wheel or resembles a gear wheel that is integrally formed with the drive member. The injection device and the drive mechanism further comprise a drive sleeve extending along a second axis, which second axis is located at a radial distance from the first axis. The drive sleeve further comprises a wheel section to engage or to mesh with the geared section of the drive member. Drive sleeve and drive member may be permanently rotationally engaged via their wheel sections or geared sections or through respective gear wheels. Via the mutually engaged wheel sections or mutually meshed geared sections a rotation of the drive sleeve induces a rotation of the drive member according to the gear ratio of the wheel sections or geared sections, respectively.

The wheel sections may each comprise a geared profile at their outer circumference. Alternatively, they may each comprise a rather even and smooth shaped outer shape, wherein the two wheel sections of the drive member and the drive sleeve are engaged in a torque transferring way by means of a band or tape. So, any mentioning of mutually engaged geared sections of drive sleeve and drive member may therefore equally relate to a torque transfer between rather even and smooth shaped wheel sections in general.

A first radial distance between first and second axes at a distal end of the drive sleeve differs from a second radial distance between first and second axes at a proximal end of the drive sleeve. The radial distance is measured perpendicular to the extension of the second axis. Since the radial distance between first and second axes differs in an axial direction it follows, that first and second axes are strictly speaking non-parallel. However, the offset from a parallel alignment of first and second axes is rather small, so that first and second axes are aligned substantially or almost parallel with respect to each other.

By varying first and second radial distances between first and second axes the overall radial extension of the arrangement of drive sleeve and drive member in particular in the axial region of their wheel sections or geared sections can be modified. In this way, the diameter of the wheel section or geared sections, in particular of gear wheel sections of drive member or drive sleeve can be modified. The diameter of wheel sections or geared sections of at least one of drive member and drive sleeve can be reduced so that the overall radial dimensions of the arrangement of drive sleeve and drive member can be reduced accordingly in order to optimize the available space inside the housing of the injection device, and in particular to reduce the outer dimensions of the housing of the injection device.

The drive member may also comprise a tubular and elongated shape. It may be axially intersected by or at least axially receive the proximal end of the piston rod. The drive member typically comprises a center axis coinciding with the first axis. Hence, at least in an initial configuration of the injection device drive member and piston rod are arranged concentrically and both extend along and align along the first axis.

According to a further embodiment the first radial distance is larger than the second radial distance. Since the radial center of the drive sleeve coincides with the second axis and since the radial center of the drive member, which may also be of tubular or sleeve-like shape coincides with the first axis at least the diameter of one of the wheel sections or geared sections of drive member and drive sleeve is reducible or is actually reduced compared to a parallel arrangement of first and second axes to enable and to support a rather compact design of the housing. Typically and according to a further embodiment the difference between first and second radial distances is larger than 0 mm but is less than 3 mm, less than 2 mm or less than 1 mm. Depending of the difference between first and second radial distances also the radial dimensions of wheel sections or geared sections of at least one of drive member and drive sleeve can be reduced. Accordingly, also a number of teeth of a size-reduced geared section can be reduced, thereby also realizing a different gear ratio between drive sleeve and drive member. A modification of the gear ratio may be compensated or counteracted by a corresponding modification of the threaded engagement of the piston rod either with the housing or with the drive member.

According to a further embodiment the injection device comprises a substantially tubular-shaped cartridge assembled inside the housing and extending along a third axis that is located at a radial distance from the second axis but which is oriented parallel to the second axis. Since the first and second axes extend at a small but distinct angle with respect to each other also the third axis extends at a non-zero angle with respect to the first axis.

The piston rod coinciding with its radial center with the first axis is hence slightly slanted or angled with regard to the longitudinal extension of the tubular-shaped cartridge. However, the piston rod typically comprising or made of a thermoplastic material exhibits a certain flexibility so that the piston rod may flex in radial direction as it advances in the distal direction so that at least its distal tip it co-aligns with the third axis and hence with the longitudinal extension of the cartridge.

According to a further embodiment the first and the third axes substantially overlap in a virtual crossing point. Due to the non-zero difference between first and second radial distances first and third axes extend at a relative offset angle equal to or smaller than 3°, equal to or smaller than 2° or equal to or smaller than 1° but larger than 0°. The virtual crossing point of first and third axes is typically located inside the injection device, hence, first and third axes virtually overlap inside the injection device. Consequently, first and third axes almost or substantially overlap but exhibit a small but distinct angular offset.

According to a further embodiment the virtual crossing point of first and third axes is located distally from a distal end of the piston rod. Typically and with the cartridge assembled inside the injection device the virtual crossing point is located inside the cartridge. It may be located inside the piston of the cartridge. Moreover, it is conceivable that the virtual crossing point is located in an axial midsection of the cartridge. Consequently and in an initial configuration of the injection device, i.e. before an initial dose of the medicament is dispensed the distal end of the piston rod may be located radially offset from the third axis. As the piston rod advances in the distal direction it approaches with its distal end to the crossing point and may then with a further distally directed displacement co-align with the third axis due to its inherent elasticity. An elastic bending or deflection of the piston rod is easily attainable as the piston rod advances in the distal direction. Since the piston rod is axially guided either in threaded or splined engagement with a radially inward facing flange portion of the housing it starts to protrude more and more in the axial distal direction from such a flange portion as it is subject to repeated dose dispensing procedures. As the piston rod advances in the distal direction it forms a cantilevered beam being easily deformable to re-align to the third axis and hence to the center axis of the cartridge.

It is to be mentioned that the angled or slightly slanted orientation of first and second axes is particularly present in an initial configuration of the injection device, i.e. prior to a first or initial dose setting or dose dispensing. As subsequent doses of the medicament have been dispensed and after the piston rod has advanced a substantial path in the distal direction, the piston rod may continuously approach an orientation of the second axis. The drive member however will remain oriented along the first axis.

In an alternative embodiment it is also conceivable, that the distal end of the piston rod is allowed to move in radial direction relative to the position of the cartridge's piston.

In another embodiment at least one of the geared sections of drive sleeve and drive member comprises a beveled gear profile. Such a beveled gear profile is beneficial when the geared sections of drive sleeve and drive member are subject to axial displacement relative to each other. It is in particular conceivable that one of drive member and drive sleeve is axially fixed or axially constrained in the housing while the other one of drive member and drive sleeve is axially displaceable relative to the housing, e.g. in order to switch the injection device from a dose setting mode to a dose dispensing mode and vice versa.

It is particularly intended, that the wheel sections or geared sections of drive sleeve and drive member remain permanently engaged. Hence, during dose setting as well as during dose dispensing the geared sections of drive member and drive sleeve mutually mesh. The axial extension of at least one of the geared sections of drive member and drive sleeve is larger than a relative axial displacement of drive member and drive sleeve. In this way, an axial displacement of the drive sleeve relative to the drive member has substantially no effect on the geared engagement of their respective geared sections.

It is of further benefit when at least one or when even both geared sections of drive sleeve and drive member comprise at least a small non-zero shaft angle, such like less than 3°, less than 2° or less than 1°. With beveled gear sections a drafted gear teeth geometry can be realized, which is beneficial when the drive sleeve or the drive member are manufactured as injection molded components. A drafted gear teeth geometry inherently supports and coincides with a beveled gear profile, which therefore maintains a full contact across the thickness or axial width of the mutually meshing geared sections. In this way, the mutual contact surface of meshed geared sections of drive member and drive sleeve can be improved with a realization of a drafted geometry of the gear teeth.

According to a further embodiment the wheel section or geared section of the drive sleeve is located near or at the proximal end of the drive sleeve. Accordingly, also the wheel section or geared section of the drive member might be located near or at the proximal end of the drive member. Moreover, the proximal end of at least one of drive member and drive sleeve may be located at or near a proximal end section of the injection device and hence in or near a proximal end section of the housing. The intended tilt of first and second axis supporting a reduced diameter of at least one of the wheel sections or geared sections of drive sleeve and drive member therefore enables a reduction of the overall radial size of a proximal housing portion.

According to another embodiment the injection device, in particular its drive mechanism further comprises a dispensing member aligned along the second axis with a shaft portion. The distal shaft portion further extends through the drive sleeve, which is hollow. The distal shaft portion is further displaceable in the distal direction relative to the drive sleeve and relative to the housing against the action of a spring member to switch the device and the drive mechanism from a dose setting mode (S) into a dose dispensing mode (D). Typically, the dispensing member further comprises a proximal button portion. The button portion serves as a proximally located dose button that is typically depressible in the distal direction by the thumb of a user in order to induce and to control a dispensing action of the injection device.

As long as the dispensing member is depressed in the distal direction the drive mechanism is in dose dispensing mode. Releasing of the dispensing member leads to a proximally directed displacement of the dispensing member under the action of the spring member, thereby transferring and returning the drug delivery device and the drive mechanism from the dose dispensing mode into the dose setting mode. Hence, a dose dispensing operation can be immediately interrupted simply by releasing the dispensing member.

According to a further embodiment the spring member comprises a distal tip overlapping with the second axis and being an axial abutment with an abutment member of the housing. The abutment member typically comprises an axially extending beam, which at its proximal end features a receptacle to receive the distal tip of the spring member. The spring member may comprise a conventional spring. Alternatively the spring member is made of an injection molded material. The spring member may therefore comprise an arbitrary shape and geometry. Furthermore, by having a distal tip, e.g. at a tapered distal end, the size of a mutual abutment area of abutment member and spring member can be minimized. In this way, frictional torque to rotate the spring member, e.g. for dose setting or for dose dispensing can be minimized. A respective driving torque, e.g. to be provided by a user, as well as inevitable wear can be minimized.

Moreover, by the mutual axial abutment between the distal and pointed or tapered tip of the spring member with a correspondingly-shaped abutment portion of the housing's abutment member also a quality of a tactile feedback to be provided by or to be transferred by the spring member can be improved.

In another embodiment the injection device and its drive mechanism further comprise a ratchet member aligned along the second axis and having a ratchet profile at a proximal end to selectively engage with a correspondingly-shaped ratchet profile at the distal end of the drive sleeve. Typically, the ratchet member is permanently axially and permanently rotationally locked to the dispensing member. Moreover, the ratchet member may be attached to a distal end of the dispensing member axially extending through and axially protruding from the distal end of the drive sleeve. The ratchet member is configured to provide an audible and/or tactile feedback signal during dose setting, in particular when the dispensing member is subject to a dose incrementing or dose decrementing rotation relative to the housing and/or relative to the drive sleeve.

Typically, during dose setting, hence when the device is in dose setting mode the drive sleeve is rotationally locked to the housing and is prevented from rotating relative to the housing. The ratchet member, in particular its ratchet profile comprises numerous ratchet teeth that sequentially engage with correspondingly-shaped ratchet teeth of the ratchet profile of the drive sleeve. During dose setting the ratchet member and the dispensing member are both subject to rotation relative to the drive sleeve. Due to the ratchet engagement obtained through the axial bias of the spring member regular click sounds or respective tactile signals are generated indicating to the user, that a dose is incremented or decremented in discrete steps. During dose setting the ratchet member and hence the dispensing member are subject to an axially directed shuttling motion, which is not only audible but which is also visible at the proximal end of the device, namely when the proximally located button portion of the dispensing member shuttles back and forth in an axial direction relative to the housing. This axial displacement due to the mutual engagement of the teeth may be only slightly larger than a clearance between the dispensing member and the ratchet member.

According to a further embodiment the spring member and the ratchet member are integrally formed. The ratchet member is axially displaceable relative to the housing and relative to the drive sleeve against the action of the spring member to switch from the dose setting mode into the dose dispensing mode. Integrally forming the ratchet member and the spring member is beneficial to reduce the overall number of components of the drive mechanism and the injection device. Moreover it may be of further benefit, when a distal end of the spring member is initially integrally connected to the ratchet member. It is then due to and during the assembly of the injection device and e.g. due to a comparatively large axial force acting on the ratchet member, that at least one or several predetermined breaking points between the distal end of the spring member and a distal end of the ratchet member break, so as to liberate and to activate the spring member.

This frangible initial connection of at least the spring member's distal end with the ratchet member is beneficial in that the spring member is deactivated until it is actually assembled inside the injection device. In this way, the rather fragile or sensitive spring member can be protected against environmental influences and can be protected against unintended damage, e.g. during transportation before getting assembled inside the injection device. Moreover, the initially integral but frangible connection of spring member and ratchet member is beneficial during assembly since the spring member is radially and/or axially confined by the ratchet member thereby facilitating the assembly of spring member and ratchet member inside the injection device.

According to another embodiment the injection device and the drive mechanism thereof further comprise a dose indicator rotationally supported on the second axis and having consecutive numbers or symbols showing up in a window of the housing when subject to a dose incrementing rotation or dose decrementing rotation with regard to the second axis during dose setting or dose dispensing. Typically, the dose indicator comprises a dose indicator sleeve or a number sleeve, wherein consecutive numbers representing the size of a dose are arranged on the outer circumference along a helical path. The dose indicator is typically axially constrained in the housing. It may be axially fixed inside the housing and is rotatable relative to the housing in this fixed axial position. Moreover, the dose indicator is selectively rotationally engageable or rotationally lockable to one of the drive sleeve and ratchet member. Typically, during dose setting or in dose setting mode the dose indicator is rotationally engaged with the ratchet member but is rotationally disengaged from the drive member. Upon switching the device into the dose dispensing mode, hence during dose dispensing the dose indicator is rotationally engaged or rotationally connected to the drive sleeve while it is decoupled or disconnected from the ratchet member.

In this way, the dose indicator is either rotationally engaged with one of drive member and ratchet member while it is disengaged from the other one of drive member and ratchet member. Switching of the device between dose setting mode and dose dispensing mode leads to a respective switching of the coupling of the dose indicator with only one of drive sleeve and ratchet member.

According to a further embodiment the injection device further comprises a gauge element that is radially sandwiched between the dose indicator and the interior of the main housing. The gauge element is typically rotationally locked to the housing but is free to move in an axial direction relative to the housing. Hence, the gauge element is splined or keyed to the housing by means of at least one radially extending protrusion of the housing or gauge element and a corresponding groove of the gauge element or housing. Due to its permanent threaded engagement with the dose indicator the gauge element travels in an axial direction as the dose indicator is subject to a rotation relative to the housing, either in dose incrementing or dose decrementing direction.

Typically, the gauge element is non-transparent and opaque to cover most numbers or symbols of the dose indicator that would otherwise show up in the window of the main housing. The gauge element further comprises at least one recess or a window through which one number or symbol of the dose indicator is visible.

The dose indicator and the gauge element further comprise mutually corresponding stop elements by way of which a maximum rotation of the dose indicator can be limited, thereby acting as a single dose limiting mechanism. The gauge element and the dose indicator may each comprise two mutually corresponding stop elements in order to limit a dose decrementing rotation of the dose indicator at the end of a dose dispensing procedure. The mutually corresponding stop elements of gauge element and dose indicator therefore provide a zero dose stop and a maximum dose stop for the drive mechanism.

The zero dose stop is operable to prevent dialing of a negative dose as well as to provide a well-defined end of a dispensing process. The maximum dose stop serves to limit the maximum amount of a dose to be set by the device.

According to a further embodiment the dose indicator is axially constrained to the housing and is threadedly engaged with the gauge element that is rotationally locked to the housing but which is axially slidably supported in the housing. Furthermore, the dose indicator comprises a click element extending in an axial direction and being located radially inside the hollow-shaped dose indicator. The click element is radially deflectable to protrude with a free end radially outwardly from the outer circumference of the dose indicator. The click element is particularly configured and adapted to provide a so called end of dose click. When mutually corresponding zero dose stops of the gauge element and the dose indicator get in abutment and engage so as to limit a further dose decrementing rotation of the dose indicator at the end of a dose dispensing procedure the click element of the dose indicator is configured to generate a well defined and distinct audible click sound to indicate to a user that the end of a dose dispensing procedure has been reached and that the process of dose injection or dose dispensing just terminated or is about to terminate.

Axial alignment as well as axial elongation of the click element is of particular benefit to reduce the sensitivity to axial tolerances of the position of the click element relative to a further component of the injection device and its drive mechanism that serves to deflect the click element radially outwardly exclusively during and/or at the beginning of the process of dose dispensing. The click element may be of arched shape and may at least partially protrude into the interior of the hollow dose indicator. Inside the hollow dose indicator at least one further component of the drive mechanism is axially guided so as to engage with the radially inwardly protruding portion of the click element and to deflect the click element, in particular its free end radially outwardly so that the outwardly deflected click element generates a well-defined and distinct clicking noise when the injection device arrives at the end of dose configuration.

According to a further embodiment the ratchet member is arranged radially inside the dose indicator and comprises a distal rim that is displaceable in the distal direction relative to the dose indicator for switching from the dose setting mode into the dose dispensing mode. During a distally directed displacement of the ratchet member during switching of the device from dose setting mode to the dose dispensing mode the distal rim of the dose indicator axially and radially engages with the click element, thereby deflecting or pivoting the free end of the click element radially outwardly in order to audibly engage with a corresponding click element of the gauge element when reaching an end of dose configuration.

Typically, the ratchet member is displaceable in the distal direction relative to the dose indicator by means of the dispensing member rigidly attached thereto. When reaching the end of dose configuration the dispensing member is to be released, so that the arrangement of dispensing member and ratchet member returns into its initial position in the proximal direction. Due to this proximally directed motion of the ratchet member relative to the dose indicator the distal rim of the ratchet member and the click element of the dose indicator disengage so that the click element returns into its radially inwardly located undeflected state, thereby disengaging from the click element of the gauge element substantially without producing any audible noise.

The axial alignment and elongation of the dose indicator click element is of particular benefit since this alignment tolerates slight deviations in the mutual alignment and arrangement of ratchet member, its distal rim and the dose indicator.

The dispensing member may be further permanently rotationally engaged with a dose dial located at a proximal end of the housing of the injection device. Hence, the dispensing member is axially slidably supported inside the main housing and may be rotatable for at least setting of a dose. The dispensing member with its distal shaft portion may be selectively rotationally lockable to the dose indicator in order to set a dose of variable size when the device is in dose setting mode. In dose dispensing mode, the dispensing member is rotationally decoupled from the dose indicator so that the dose indicator is enabled to return into a zero dose position without inducing a rotation of the dispensing member.

When in dose dispensing mode the dispensing member and hence the dose dial may be rotatable relative to the main housing. Since the dispensing member is rotationally disengaged from driving components of the drive mechanism during dose dispensing, any rotation of either the dose dial or the dispensing member has no measurable effect on the operation of the injection device.

According to a further embodiment the drive sleeve is permanently rotationally coupled to the piston rod and is further rotationally biased by a mainspring. The drive sleeve is further rotationally locked to the housing when in dose setting mode and is rotationally released from the housing in dose dispensing mode. Hence, the drive sleeve is exclusively rotatable relative to the housing during dose dispensing for advancing the piston rod in the distal direction. The mainspring, acting as a driving spring and acting as a mechanical energy storage means is permanently engaged and coupled to the drive sleeve. It is typically pre-tensed or preloaded to such a degree, that the mechanical energy stored in the mainspring is sufficient to displace the piston rod from an initial proximal position into a final distally located position, in which the entirety of the medicament initially provided in the cartridge has been dispensed.

The mainspring is therefore a preloaded spring. When the injection device is configured and designed as a reusable device the mainspring is rechargeable during a reset operation. The permanent coupling of the drive sleeve with the piston rod and with the mainspring and the selective coupling and rotational locking of drive sleeve and main housing is beneficial in terms of a user friendly handling of the injection device. Typically, the rotational lock between drive sleeve and main housing in dose setting mode allows a user-induced dose setting without acting against the preloaded mainspring. Dose setting is therefore rather easy and does not require biasing of the mainspring. It is only due to a distally directed displacement of the drive sleeve, typically by means of and through interaction with the dispensing member, that the drive sleeve rotationally disengages from the housing and is liberated to rotate under the action of the mainspring.

In the course of a combined distally directed displacement of dispensing member and drive sleeve for dispensing of a dose, the dispensing member is rotationally decoupled from the dose indicator and the drive sleeve is rotationally coupled or rotationally locked to the dose indicator. In this way, the rotating drive sleeve induces a corresponding rotation of the dose indicator in a dose decrementing direction in order to return the dose indicator into an initial configuration.

In another embodiment the ratchet member is rotationally locked to the dose indicator when in dose setting mode. The ratchet member is further rotationally released from the dose indicator when in dose dispensing mode. Switching of the injection device from the dose setting mode into the dose dispensing mode axially displaces the ratchet member relative to the dose indicator, thereby releasing a torque-proof clutch between ratchet member and dose indicator.

The ratchet member is displaceable in the distal direction when switching the injection device in dose dispensing mode. This distally directed displacement is obtained through the permanent and axial coupling of ratchet member and dispensing member. Selective rotational interlocking or rotational engagement of ratchet member and dose indicator provides a dose incrementing rotation of the dose indicator during dose setting. A decoupling of ratchet member and dose indicator for dose dispensing and a rotational engagement of dose indicator and drive sleeve during dose dispensing provides a dose decrementing rotation of the dose indicator during dispensing of a dose, thereby returning to a zero dose configuration.

According to a further embodiment the dispensing member is transferable in axial abutment with the drive sleeve to displace the drive sleeve into a distal dispense position, in which the drive sleeve is rotationally released from the main housing and from the dose indicator. The drive sleeve and the dispensing member comprise mutually corresponding radially extending shoulder portions that allow and support a rotation of the drive sleeve relative to the dispensing member when the injection device is in dose dispensing mode. Typically, the drive sleeve comprises a proximally facing abutment portion axially engaging with a distally facing abutment portion of the dispensing member. The abutment portions typically extending radially on the outer and inner circumference of drive sleeve and dispensing member, respectively. Distally displacing the dispensing member relative to the housing therefore advances the drive sleeve in the distal direction, thereby releasing the rotational interlock between the drive sleeve and the main housing.

In dose setting mode there is an axial gap between the mutually corresponding shoulder portions of drive sleeve and dispensing member, in particular between the proximally facing abutment portion of the drive sleeve and the distally facing abutment portion of the dispensing member. In this way and in the course of depressing the dispensing member in the distal direction relative to the housing the ratchet engagement of ratchet member and drive sleeve is disengaged before the mutually corresponding abutment portions of drive sleeve and dispensing member get in axial abutment. In this way a coupling or a ratchet engagement between drive sleeve and ratchet member is disengaged before the torque-proof clutch between drive sleeve and housing is disengaged.

Mutual engagement of dispensing member and drive sleeve is purely axial. While the drive sleeve is displaced in the distal direction by means of the abutment with the distally advancing dispensing member, the drive sleeve is free to rotate relative to the housing and relative to the dispensing member.

Moreover, before the drive sleeve disengages from the housing it engages in a torque-proof way with the dose indicator. A selective engagement and disengagement of the drive sleeve and the dose indicator is obtained through the axial displacement of the drive sleeve relative to the housing and hence relative to the dose indicator which is axially constrained to and inside the housing. For this purpose, the drive sleeve intersecting or at least axially extending into a proximal end of the dose indicator comprises a geared, splined or keyed structure at its outer circumference to engage and to disengage with a correspondingly-shaped geared, splined or toothed structure at the inside facing sidewall portion of the dose indicator. The mutually corresponding toothed portions are arranged at such axial positions and comprise an axial elongation such that a torque-proof clutch formed by these toothed portions engages before a torque-proof clutch of housing and drive sleeve disengages.

The injection device is particularly implemented as a so called auto-injector, wherein the mainspring serves as a mechanical energy storage, by way of which a driving or dispensing force or torque is provided for the injection of the medicament. The mainspring is typically preloaded to such an extent, that the mechanical energy stored therein is sufficient to expel the entirety of the medicament located inside the cartridge. Between consecutive dispensing actions a biasing or recharging of the mainspring is therefore not required. During dose setting a user does not have to provide a torque against the action of a spring element for eventually biasing the same. It is only during an optional reset operation that the mainspring or drive spring has to be charged and that the piston rod is retracted into its initial proximal position.

In the present context, the distal direction points in the direction of the dispensing end of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in the distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO: 1).

Exendin-4 derivatives are for example selected from the following list of compounds:

```
                                                         (SEQ ID NO: 2)
H-(Lys)4-des Pro36, des Pro37 Exendin-4(1-39)-NH2, (SEQ ID NO: 3)
H-(Lys)5-des Pro36, des Pro37 Exendin-4(1-39)-NH2, (SEQ ID NO: 4)
des Pro36 Exendin-4(1-39), (SEQ ID NO: 5)
des Pro36 [Asp28] Exendin-4(1-39), (SEQ ID NO: 6)
des Pro36 [IsoAsp28] Exendin-4(1-39), (SEQ ID NO: 7)
des Pro36 [Met(O)14, Asp28] Exendin-4(1-39), (SEQ ID NO: 8)
des Pro36 [Met(O)14, IsoAsp28] Exendin-4(1-39), (SEQ ID NO: 9)
des Pro36 Asp28] Exendin-4(1-39), (SEQ ID NO: 10)
des Pro36 IsoAsp28] Exendin-4(1-39), (SEQ ID NO: 11)
des Pro36 [Met(O)14 Trp(O2)25, Asp28] Exendin-4(1-39), (SEQ ID NO: 12)
des Pro36 [Met(O)14 Trp(O2)25, IsoAsp28] Exendin-4(1-39);
or (SEQ ID NO: 5)
des Pro36 [Asp28] Exendin-4(1-39), (SEQ ID NO: 6)
des Pro36 [IsoAsp28] Exendin-4(1-39), (SEQ ID NO: 7)
des Pro36 [Met(O)14, Asp28] Exendin-4(1-39), (SEQ ID NO: 8)
des Pro36 [Met(O)14, IsoAsp28] Exendin-4(1-39), (SEQ ID NO: 9)
des Pro36 Asp28] Exendin-4(1-39), (SEQ ID NO: 10)
des Pro36 IsoAsp28] Exendin-4(1-39), (SEQ ID NO: 11)
des Pro36 [Met(O)14 Trp(O2)25, Asp28] Exendin-4(1-39), (SEQ ID NO: 12)
des Pro36 [Met(O)14 Trp(O2)25, IsoAsp28] Exendin-4(1-39),
``` wherein the group -Lys6-NH2 may be bound to the C-terminus of the Exendin-4 derivative;
or an Exendin-4 derivative of the sequence des Pro36 Exendin-4(1-39)-Lys6-NH2 (SEQ ID NO: 13)
(AVE0010), H-(Lys)6-des Pro36 [Asp28] Exendin-4(1-39)-Lys6-NH2, (SEQ ID NO: 14)

des Asp28 Pro36, Pro37, Pro38Exendin-4(1-39)-NH2, (SEQ ID NO: 15)

H-(Lys)6-des Pro36, Pro38 [Asp28] Exendin-4(1-39)-NH2, (SEQ ID NO: 16)

H-Asn-(Glu)5des Pro36, Pro37, Pro38 [Asp28] Exendin-4(1-39)-NH2, (SEQ ID NO: 17)

des Pro36, Pro37, Pro38 [Asp28] Exendin-4(1-39)-(Lys)6-NH2, (SEQ ID NO: 18)

H-(Lys)6-des Pro36, Pro37, Pro38 [Asp28] Exendin-4(1-39)-(Lys)6-NH2, (SEQ ID NO: 19)

H-Asn-(Glu)5-des Pro36, Pro37, Pro38 [Asp28] Exendin-4(1-39)-(Lys)6-NH2, (SEQ ID NO: 20)

H-(Lys)6-des Pro36 Asp28] Exendin-4(1-39)-Lys6-NH2, (SEQ ID NO: 21)

H-des Asp28 Pro36, Pro37, Pro38 [Trp(O2)25] Exendin-4(1-39)-NH2, (SEQ ID NO: 22)

H-(Lys)6-des Pro36, Pro37, Pro38 [Trp(O2)25, Asp28] Exendin-4(1-39)-NH2, (SEQ ID NO: 23)

H-Asn-(Glu)5-des Pro36, Pro37, Pro38 [Trp(O2)25, Asp28] Exendin-4(1-39)-NH2, (SEQ ID NO: 24)

des Pro36, Pro37, Pro38 [Trp(O2)25], Asp28] Exendin-4(1-39)-(Lys)6-NH2, (SEQ ID NO: 25)

H-(Lys)6-des Pro36, Pro37, Pro38 [Trp(O2)25, Asp28] Exendin-4(1-39)-(Lys)6-NH2, (SEQ ID NO: 26)

H-Asn-(Glu)5-des Pro36, Pro37, Pro38 [Trp(O2)25, Asp28] Exendin-4(1-39)-(Lys)6-NH2, (SEQ ID NO: 27)

H-(Lys)6-des Pro36 [Met(O)14, Asp28] Exendin-4(1-39)-Lys6-NH2, (SEQ ID NO: 28)

des Met(O)14 Asp28 Pro36, Pro37, Pro38 Exendin-4(1-39)-NH2, (SEQ ID NO: 29)

H-(Lys)6-desPro36, Pro37, Pro38 [Met(O)14, Asp28] Exendin-4(1-39)-NH2, (SEQ ID NO: 30)

H-Asn-(Glu)5-des Pro36, Pro37, Pro38 [Met(O)14, Asp28] Exendin-4(1-39)-NH2, (SEQ ID NO: 31)

des Pro36, Pro37, Pro38 [Met(O)14, Asp28] Exendin-4(1-39)-(Lys)6-NH2, (SEQ ID NO: 32)

H-(Lys)6-des Pro36, Pro37, Pro38 [Met(O)14, Asp28] Exendin-4(1-39)-(Lys)6-NH2, (SEQ ID NO: 33)

H-Asn-(Glu)5 des Pro36, Pro37, Pro38 [Met(O)14, Asp28] Exendin-4(1-39)-(Lys)6-NH2, (SEQ ID NO: 34)

H-Lys6-des Pro36 [Met(O)14, Trp(O2)25, Asp28] Exendin-4(1-39)-Lys6-NH2, (SEQ ID NO: 35)

```
                                                           (SEQ ID NO: 36)
H-des Asp28 Pro36, Pro37, Pro38 [Met(O)14, Trp(O2)25] Exendin-4(1-39)-NH2, (SEQ ID NO: 37)
H-(Lys)6-des Pro36, Pro37, Pro38 [Met(O)14, Asp28] Exendin-4(1-39)-NH2, (SEQ ID NO: 38)
H-Asn-(Glu)5-des Pro36, Pro37, Pro38 [Met(O)14, Trp(O2)25, Asp28]

Exendin-4(1-39)-NH2, (SEQ ID NO: 39)
des Pro36, Pro37, Pro38 [Met(O)14, Trp(O2)25, Asp28] Exendin-4(1-39)-

(Lys)6-NH2, (SEQ ID NO: 40)
H-(Lys)6-des Pro36, Pro37, Pro38 [Met(O)14, Trp(O2)25, Asp28] Exendin- 4(S1-39)-(Lys)6-NH2, (SEQ ID NO: 41)
H-Asn-(Glu)5-des Pro36, Pro37, Pro38 [Met(O)14, Trp(O2)25, Asp28] Exendin-4(1-39)-(Lys)6-NH2;
``` or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, a non-limiting embodiment of the injection device with its drive mechanism is described in detail by making reference to the drawings, in which:

FIG. 9 shows a pre-assembly configuration of the ratchet member with integrated spring member, FIG. 10 shows the ratchet member according to FIG. 9 in dose setting mode, FIG. 11 shows the configuration of the ratchet member and its integrated spring member in dose dispensing mode, FIG. 16 shows a cross section through a distal portion of the device in dose setting mode after setting of a dose, FIG. 17 shows the distal end of the device when in dose dispensing mode, FIG. 18 shows the section according to FIGS. 16 and 17 when the dose indicator returns into the zero dose configuration at the end of a dose dispensing procedure and FIG. 19 is indicative of the end of dose configuration, in which the free end of the deflected click element of the dose indicator reaches a recess in the inside facing sidewall portion of the gauge element.

DETAILED DESCRIPTION

Figure 1:
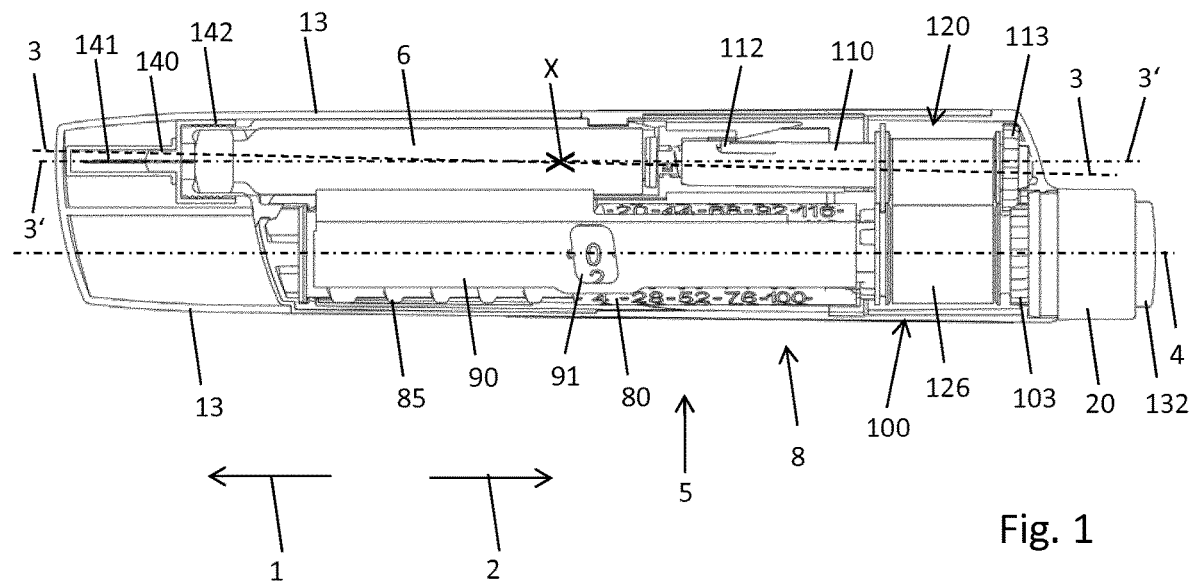
FIG. 1 shows a partially transparent side view of the injection device.
Figure 2:
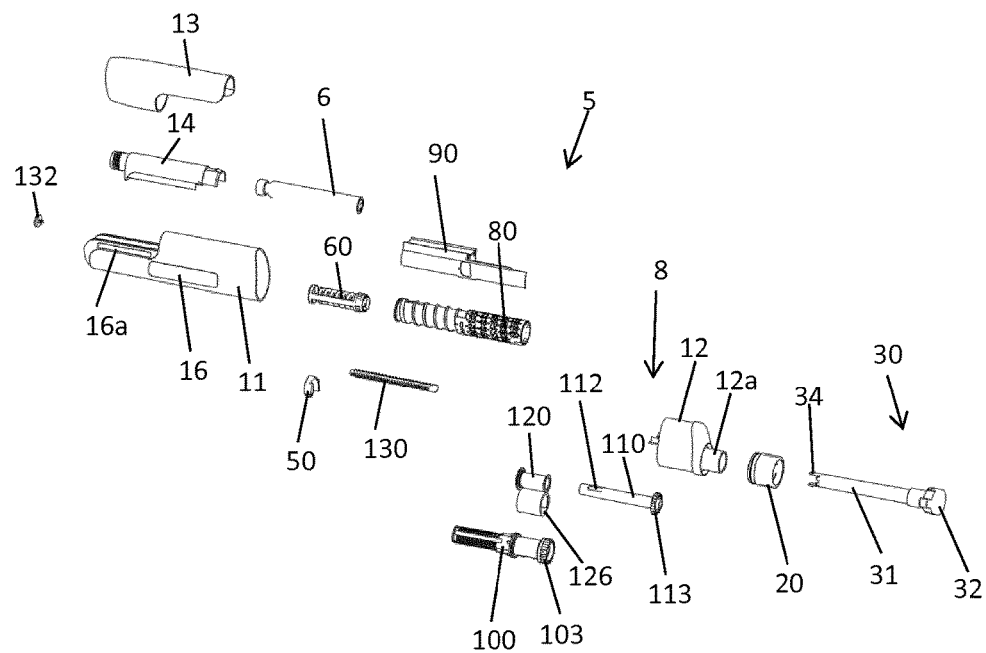
FIG. 2 shows an exploded and perspective view of the components of the injection device.
Figure 5:
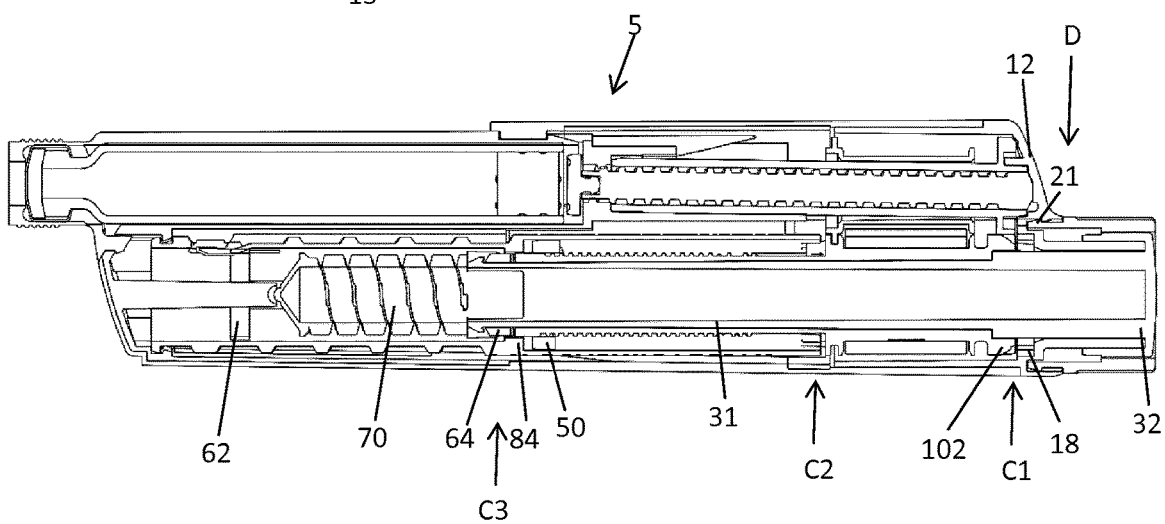
FIG. 5 shows the device according to FIG. 3 in dose dispensing mode.

The injection device 5 as illustrated in FIG. 1 is configured as an all mechanically implemented auto-injector. It comprises a housing 10 featuring a main housing 11 of elongated shape and extending in an axial direction. The main housing 11 comprises a distal end facing in a distal direction 1 and further comprising a proximal end facing in a distal direction 2. The housing 10 comprises a proximal housing portion 12 that is connectable with a proximal end of the main housing 11. The proximal housing portion 12 serves as a kind of a lid closing the tubular-shaped main housing 11 in proximal direction 2. As shown in FIG. 2, the proximal housing portion 12 comprises a proximally extending socket portion 12a that serves as a support and a bearing for a dose dial 20 rotationally supported on the housing 10 and axially fixed thereto by means of at least one snap member 21 as shown in FIG. 5.

In distal direction 1 the main housing 11 terminates with a distal front face from which a cartridge holder 14 axially protrudes. As it is apparent from FIG. 1, the cartridge holder 14 comprises a threaded socket 14a to threadedly engage with a needle hub 142 of a piercing assembly 140 that comprises a double-tipped injection needle 141. The cartridge holder 14 comprises a through opening at its distal front face to receive the proximal end of the injection needle 141. When not in use the distal end of the injection device 5, in particular the cartridge holder 14 is covered by a detachable protective cap 13.

Figure 3:
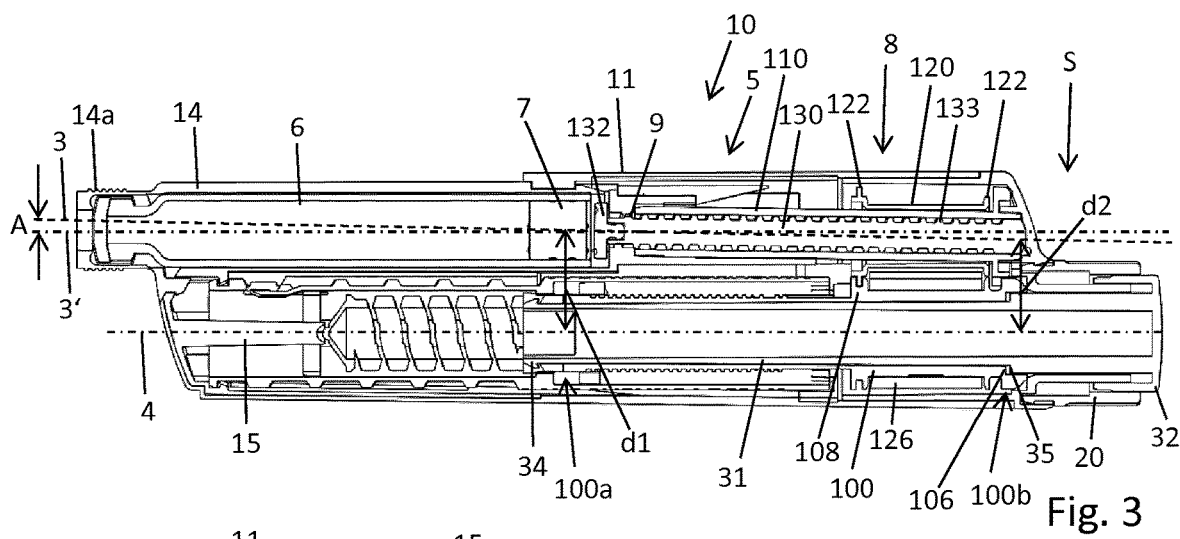
FIG. 3 is a longitudinal cross-section through the injection device in dose setting mode.

As it is apparent from FIGS. 1-5 there are provided two principal axes 3, 4 along which almost all mechanical components of the injection device 5 are aligned. Almost all mechanical components of the injection device 5 are located concentrically about one of the two principal axes 3, 4. The first and second axes 3, 4 are separated by a radial distance. They extend substantially parallel with respect to each other with a slight angular offset as shown in FIG. 3. Along the first axis 3 there are aligned the elongated piston rod 130 that is rotationally engaged with a co-aligned sleeve-shaped drive member 110. Typically, the piston rod 130 is keyed or splined with the drive member 110. The drive member 110 typically comprises a radially inwardly extending protrusion that is engaged with an axially extending groove on the outer circumference of the piston rod 130. Furthermore, the piston rod 130 comprises an outer thread 133 by way of which it is threadedly engaged with a threaded through opening of a radially inwardly extending flange portion 9 of the main housing 11. A rotation of the drive member 110 therefore leads to a corresponding rotation of the piston rod 130 relative to the housing 10, which due to the threaded engagement of piston rod 130 and housing 10 or main housing 11 leads to a distally directed displacement of the piston rod 130 thereby exerting a distally directed pressure to the piston 7 of the cartridge 6.

In an alternative embodiment it is also conceivable, that the piston rod 130 is in splined engagement with the main housing 11, i.e. the piston rod 130 is free to be axially displaced relative to the main housing 11 but is for instance threadedly engaged with the hollow drive member 110.

The drive member 110 is in permanent rotational engagement with a drive sleeve 100 through a geared engagement. The drive sleeve 100 is arranged radially adjacent to the drive member 110. The geared engagement of drive sleeve 100 and drive member 110 is even invariant to slight axial displacement of the drive sleeve 100 relative to the drive member 110. As can be seen from FIGS. 3, 5, and 13 the drive sleeve 100 is arranged along the second principal axis 4. Concentrically arranged with this second axis 4 there is further provided a sleeve-shaped dispensing member 30, a dose dial 20, a gauge element 90, a dose indicator 80 and a ratchet member 60.

The dose dial 20 is axially fixed to the housing 10, in particular to the proximal housing portion 12, e.g. by way of mutually engaging latch or clip members 21, e.g. positively locked and positively engaged with a corresponding recess of the proximal housing portion 12. In this way, the dose dial 20 is rotatable relative to the housing 10. The dose dial 20 is permanently rotationally locked to the dispensing member 30 having a proximal button portion 32 at least slightly proximally protruding from the proximal end of the dose dial 20 when in dose setting mode (S).

The dispensing member 30 further has a shaft portion 31 extending along the second axis 4. The dispensing member 30 comprises at least one, typically several radially outwardly biased snap members 34 at its distal end to permanently axially engage with correspondingly shaped recesses of the ratchet member 60. In this way, the dispensing member 30 and the ratchet member 60 are permanently axially and rotationally locked to each other. Axial displacement as well as a rotation of the dispensing member 30 equally transfers to the ratchet member 60; and vice versa.

Figure 7:
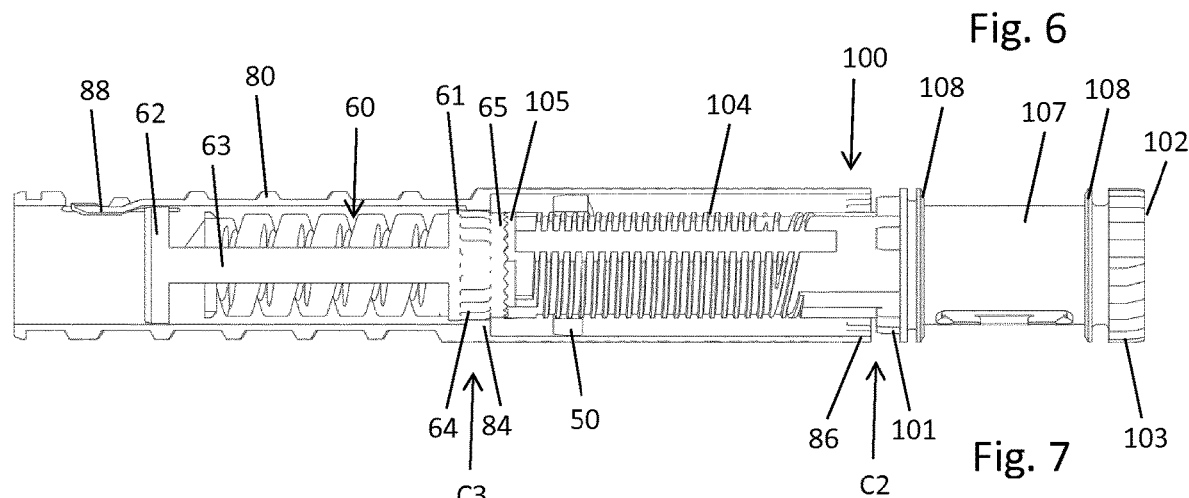
FIG. 7 is a side view of the ratchet member in engagement with the dose indicator and the drive sleeve.

The drive sleeve 100 further has a detent structure 102 at a proximally facing socket portion or at a proximal end engaging with a correspondingly-shaped detent structure 18 of the housing 10 as shown in FIG. 5. The detent structures 18, 102 form a first clutch C1 by way of which the drive sleeve 100 is rotationally locked to the housing 10 when in the proximal dose setting position (S). The drive sleeve 100 further comprises a geared section 103 near or at its proximal end as shown in FIGS. 2 and 7.

The drive sleeve 100 is axially intersected by the shaft portion 31 of the dispensing member 30. The drive sleeve 100 further comprises a threaded section 104 near its distal end which is threadedly engaged with a correspondingly threaded last dose limiting member 50 as shown in FIG. 7. The last dose limiting member 50 is furthermore in splined engagement with the inside facing portion of the dose indicator 80 through which the drive sleeve 100 axially extends. During dose setting the dose indicator 80 rotates relative to the rotationally locked drive sleeve 100, thereby inducing a corresponding rotation of the last dose limiter 50, which upon the threaded engagement with the drive sleeve 100 travels in an axial direction, e.g. in the proximal direction as a dose of increasing size is set.

There are provided mutually corresponding stop features on the outer circumference of the drive sleeve 100 and the last dose limiter 50. When reaching an end of content configuration, in which the dose to be set would exceed the amount of medicament left in the cartridge, the last dose limiter 50 is blocked from rotating further relative to the drive sleeve 100 thereby inhibiting any further dose incrementing rotation of the dose dial 20.

Figure 4:
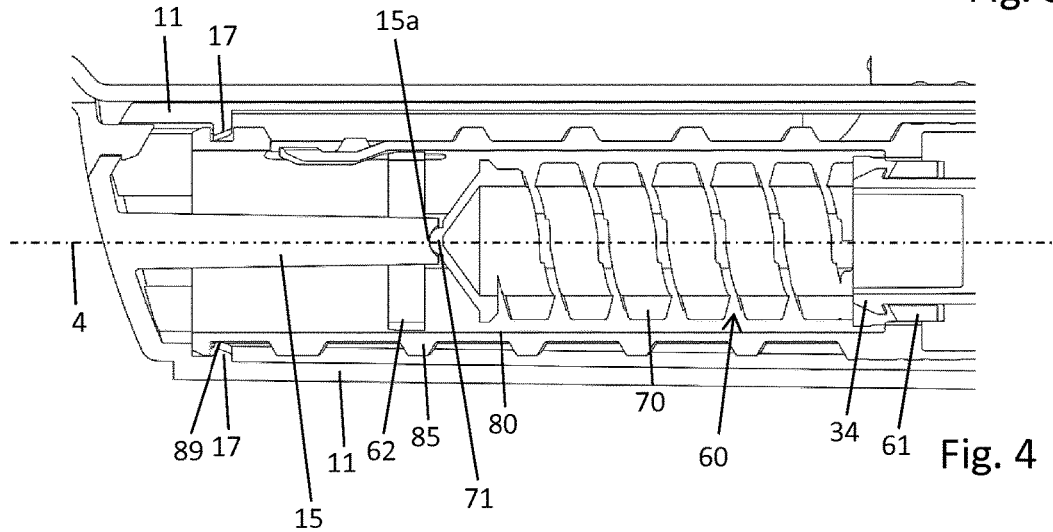
FIG. 4 shows an enlarged portion of the device according to FIG. 3.

The dose indicator 80 is axially constrained and hence axially locked to the housing 10. This is achieved by a radially inwardly extending protrusion 17 of the main housing 11 engaging with a correspondingly shaped annular and circumferential groove 89 of the dose indicator 80 as shown in FIG. 4. In this way, the dose indicator 80 and the housing 10 are permanently axially engaged and the dose indicator 80 is free to rotate relative to the housing with regard to the second axis 4.

As it is shown in detail in FIG. 3 the first axis 3 extends at a slight offset angle A with respect to the second axis 4. Hence, a first radial distance d1 between first and second axes 3, 4 at a distal end 100a of the drive sleeve 100 differs from a second radial distance d2 between first and second axes 3, 4 at a proximal end 100b of the drive sleeve 100. In the present embodiment, the first radial distance d1 is larger than the second radial distance d2. Hence, the radial distance between first and second axes 3, 4 is smaller at the proximal end of the injection device 5, compared to a middle section of the injection device or compared to an axial position, where the distal end 100a of the drive sleeve 100 is located. This non-parallel but slightly converging alignment of first and second axes 3, 4 towards the proximal direction 2 has the beneficial effect, that the center distance d2 between drive member 110 and drive sleeve 100 in the region of their mutually engaged geared sections 103, 113 is reduced compared to a radial center distance d1 at the distal end 100a of the drive sleeve 100.

Figure 12:
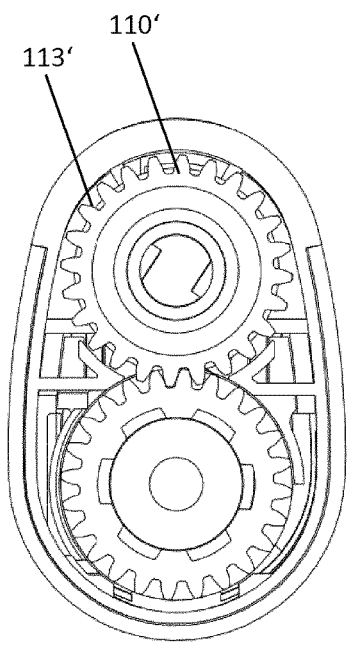
FIG. 12 is a cross section through a proximal end section of a comparative injection device, wherein first and third axes are aligned parallel.
Figure 13:
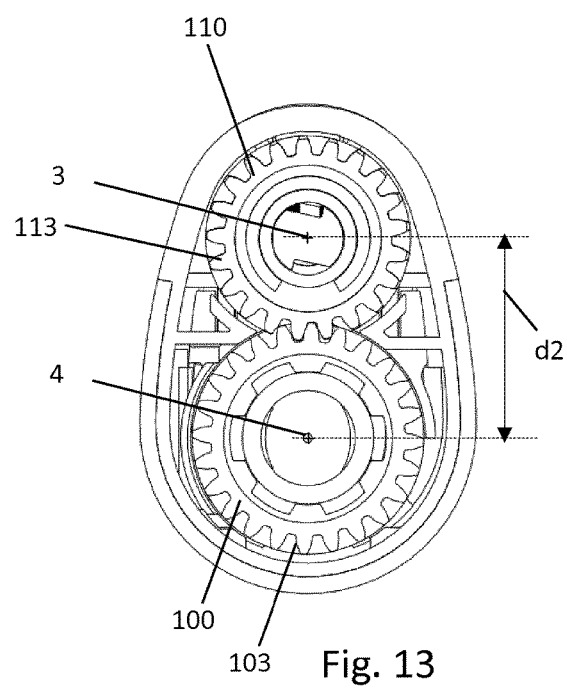
FIG. 13 shows a cross section according to FIG. 12 but of an embodiment, wherein first and third axes are slightly tilted.

A comparison of the cross section according to FIG. 13 with a parallel arrangement of first and second axes 3, 4 as illustrated in FIG. 12, reveals, that the radial extension of at least one of the geared sections 103, 113 of drive sleeve 100 and drive member 110 can be reduced. Especially a comparison of the geared sections 113 and 113' of FIGS. 13 and 12 shows that the number of teeth of the geared section 113 is reduced compared to the number of teeth of the geared section 113' of a drive member 110' that is arranged parallel to the second axis 4 as shown in FIG. 12.

The smaller and size reduced radial dimension of at least one of the geared sections 103, 113 provides the possibility to reduce the overall radial dimensions of the housing 10 of the injection device 5. Consequently, a rather compact design of an injection device 5 can be provided, especially at a proximal end thereof which is to be gripped and held in the hand of a user.

To avoid increasing the radial dimensions near a distal end of the injection device 5 the cartridge is assembled inside the housing 10 in particular inside the cartridge holder 14 and extends along a third axis 3' at a radial distance from the second axis 4 but parallel to the second axis 4. Consequently, first axis 3 and third axis 3' almost coincide but are oriented at the offset angle A as can be seen from FIG. 3. Consequently first and third axes 3, 3' coincide or cross in a virtual crossing point X. The virtual crossing point X is located distally from a distal end of the piston rod 130. It is typically located inside the cartridge 6 or inside the piston 7 of the cartridge 6. As subsequent dispensing procedures take place the piston rod 130 with a bearing 132 or pressure piece advances in distal direction 1. Then, the piston rod 130 extends along the first axis 3 and tends to cross the third axis 3'.

Figure 14:
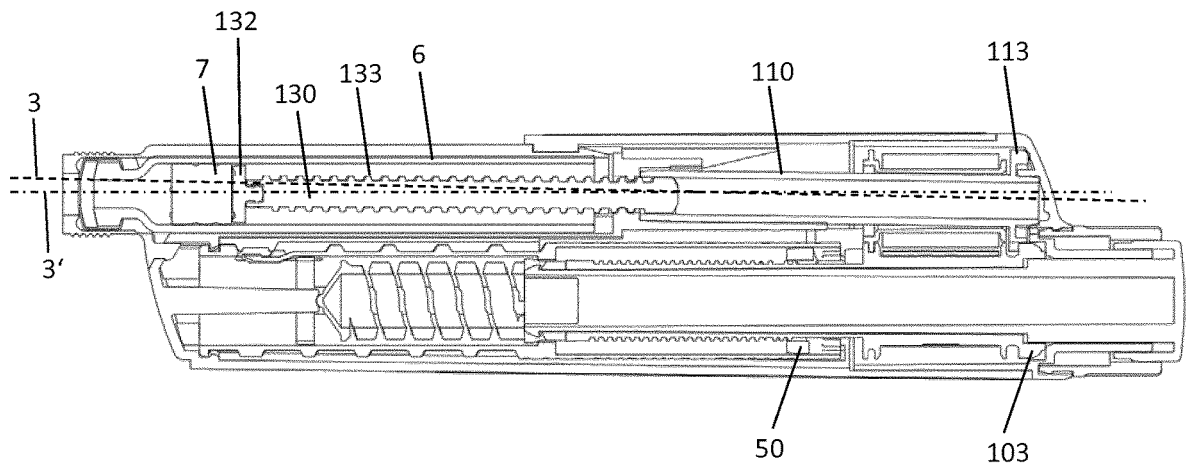
FIG. 14 shows the device according to FIG. 3 in an end of content configuration with a slightly bended piston rod.

However and since the piston rod 130, in particular its bearing 132 is radially confined inside the tubular-shaped barrel of the cartridge 6 at least its distal end experiences a co-alignment with the third axis 3' as the distally directed displacement of the piston rod continues. Moreover, as the piston rod 130 advances distally its distal end departs more and more from the threaded flange portion 9 and therefore resembles a cantilever arm the free and distal end of which being easily deflectable in radial direction so that the distal end of the piston rod 130 co-aligns and coincides with the third axis 3' as illustrated in FIG. 14.

Figure 6:
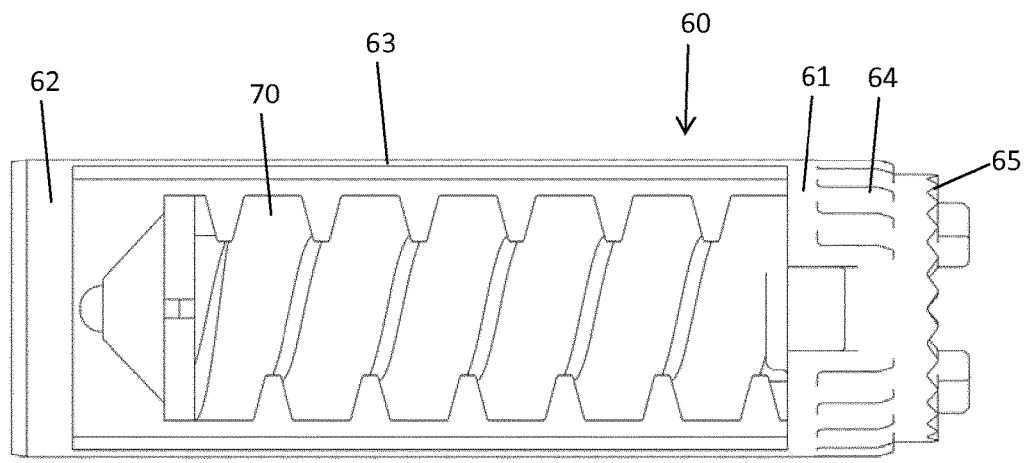
FIG. 6 is an isolated side view of the ratchet member.

The ratchet member 60 as separately shown in FIG. 6 comprises a proximal rim 61 and a distal annular rim 62 that are interconnected by at least one axially extending bridging portion 63. Typically, there are provided two radially oppositely located rod-like bridging portions 63 interconnecting the proximal and distal rims 61, 63. The proximal rim 61 comprises a toothed profile 64 on its radially outwardly facing circumference to selectively engage with the correspondingly toothed profile 84 of the dose indicator 80 as shown in FIG. 7. In this way, ratchet member 60 and dose indicator 80 form a third torque-proof clutch C3 that is releasable through a distally directed displacement of the ratchet member 60 relative to the housing 10 and hence relative to the dose indicator 80.

Figure 8:
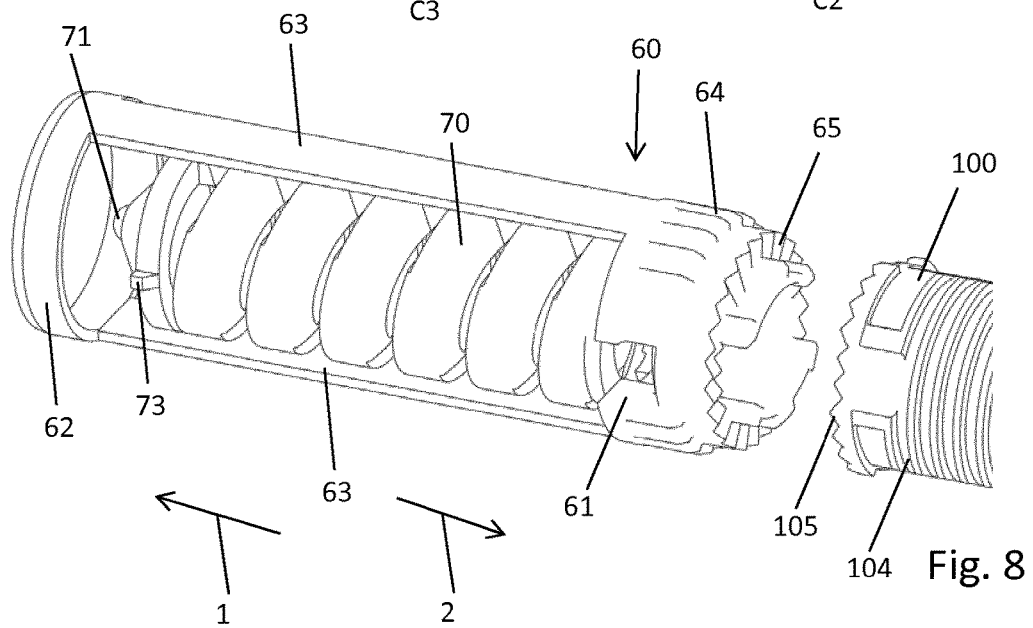
FIG. 8 shows the mutually corresponding ratchet profiles at the proximal and distal end faces of the ratchet member and the drive sleeve, respectively.

The proximally facing surface of the proximal rim 61 further comprises a ratchet profile 65 that is selectively engageable with a correspondingly-shaped ratchet profile 105 located at a distal end face of the drive sleeve 100 as shown in FIGS. 7 and 8. In addition, the ratchet member 60 is axially biased by a spring member 70 that is integrally formed with the ratchet member 60 and which axially extends between the proximal rim 61 and the distal rim 62. The ratchet member 60 and the spring member 70 are manufactured by injection molding, in particular by an injection molded thermoplastic material. The thermoplastic and injection molded spring member 70 comprises a helical structure that is axially compressible to provide an axial spring force. As shown in detail in FIG. 4, the spring member 70 has a tapered distal end featuring a knob-shaped distal tip 71. By means of this distal tip 71 coinciding with the second axis 4 the spring member 70 axially abuts with an abutment member 15 of the housing 10. The abutment member resembling a post extending proximally from a distal front face of the housing features a bearing 15a to accommodate the knob-shaped distal tip 71 of the spring member 70.

The almost pointed abutment between abutment member 15 and distal tip 71 of the spring member 70 is beneficial in that a contact surface between spring member 70 and abutment member 15 is minimized. Moreover, the mutual abutment coincides with the second axis 4 the spring member 70 and hence the ratchet member 60 is easily rotatable relative to the housing 10 with a minimum of friction. This friction reduced abutment is of particular benefit during setting of a dose as well as to provide an improved audible and/or tactile feedback during dose setting.

As shown in FIG. 6 the spring member 70 is integrally formed with a proximal end section with the proximal rim 61 of the ratchet member 60. In an initial configuration and prior to an assembly of the ratchet member 60 inside the injection device 5 also a distal end of the spring member 70 is integrally formed and integrally connected to the distal rim 62 of the ratchet member 60. In this initial state as shown in FIG. 9 the spring member 70 and in particular its distal end is substantially deactivated. It is hence hindered to move or to swing relative to the ratchet member 60. This makes the arrangement of ratchet member 60 and spring member 70 rather robust against environmental influences, especially during transportation to an assembly line of the injection device 5.

During assembly a rather larger axial force above a predefined threshold is applied in the distal direction towards the ratchet member 60. When the distal tip 71 of the spring member 70 is already in axial abutment with the abutment member 15 the frangible connection 72, in particular radially outwardly extending lobes 73 of the spring member 70, that are initially interconnected with the distal rim 62, disconnect and break so as to liberate and to activate the spring member 70. The spring member 70 then relaxes into the shape as shown in FIG. 10 wherein the distal tip 71 is located proximally compared to the axial position of the distal rim 62.

When in dose setting mode and when the ratchet member 60 is subject to an axial and distal displacement relative to the housing the spring member 70 is compressed as shown in FIG. 11 against a restoring force.

As the dispensing member 30 is released it is due to the action and effect of the spring member 70, that the proximal rim 61 and hence the ratchet member 60 returns into its initial dose setting position in proximal direction 2.

Figure 15:
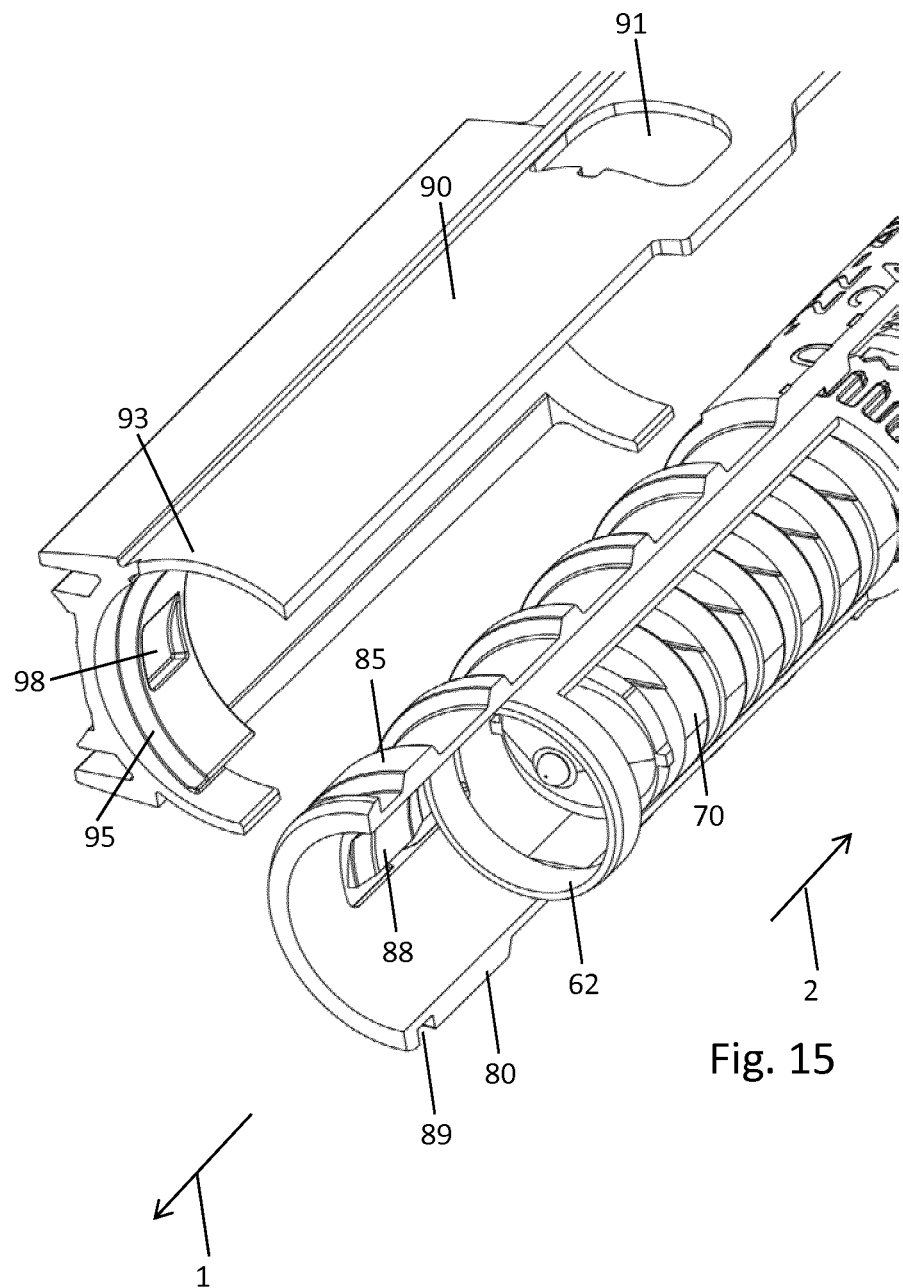
FIG. 15 shows an isolated and perspective illustration of ratchet member, dose indicator and gauge element.

In FIG. 15 there are shown the sleeve-shaped dose indicator 80 as well as the gauge element 90. The gauge element 90 comprises an elongated and opaque structure with a dose indicating window 91 through which dose indicating numbers of the dose indicator 80 are visible from outside the injection device 5. The gauge element 90 is splined to the interior of the main housing 11. It is rotationally locked to the main housing 11 but is free to slide in the axial direction relative to the main housing 11. A distal portion of the dose indicator 80 comprises a threaded or helical section 85 that mates and engages a helical section 95 on the inside facing surface portion of the gauge element 90. A rotation of the dose indicator 80 therefore leads to an axial displacement of the gauge element 90.

The dose indicator 80 further comprises a zero dose stop as well as a maximum dose stop at axially opposite end sections of the helical section 85. When reaching a minimum or maximum dose configuration the dose indicator 80 with its stops tangentially and/or axially abuts with correspondingly-shaped stop features of the gauge element 90. In addition and as shown in FIGS. 16-23 the dose indicator 80 comprises a click element 88 to audibly engage with a correspondingly-shaped click element 98 of the gauge element 90 when reaching an initial, hence a zero dose configuration at the end of a dispensing procedure, thereby audibly indicating to a user that the process of injection has terminated.

The opaque gauge element 90 is radially sandwiched between the dose indicator 80 and a dose indicating window 16 of the main housing 11 as it is apparent from FIGS. 1 and 15. During a dose setting, in particular during a dose incrementing rotation of the dose indicator 80, the gauge element 90 travels in proximal direction 2, thereby displacing the window 91 to reveal consecutively increasing numbers of the rotating dose indicator 80. At the same time also a distal portion 93 of the gauge element 90 travels in proximal direction 2 which is visible through another window 16a of the main housing 11 as indicated in FIG. 2. The distal portion 93 of the gauge element 90 provides an additional visual user feedback of the actual dose position of the device. This is of particular benefit during dose dispensing, namely when the gauge element 90 returns into its distal position.

As the gauge element 90 moves in the proximal direction during setting of a dose it reveals a further surface underneath. The axial size of the windows 16, 16a is directly correlated to the maximum size of a dose to be set and dispensed. During the dose dispensing procedure, the progress of dose dispensing is immediately apparent through a comparison of the actual position of the gauge element window 91 within the window 16 or by the axial position of the distal edge of the distal portion 93 inside the window 16a.

A visible surface portion of the gauge element 90 visible in the widow 16a therefore provides an analogue indication or analogue gauge of the size of the dose dialed, which helps to improve overall handling of the device 5 and which helps to improve patient safety.

The analogue gauge provided by the additional window 16a and the distal portion 93 of the gauge element 90 is of particular use during dispensing of a dose. The number digit display provided by the rotating dose indicator 80 may change too quickly for individual dose position markings to be legible. It may be therefore difficult for the user to estimate the rate at which the dose is actually dispensed and the amount of medicament still to be dispensed.

In the following setting of a dose is described. For setting of a dose a user starts to rotate the dose dial 20 in a dose incrementing direction, e.g. clockwise relative to the housing 10. This causes the dispensing member 30 to rotate since dose dial 20 and dispensing member 30 are in permanent rotational interlock. The rotation of the dispensing member 30 equally transfers to a rotation of the ratchet member 60, which due to the ratchet engagement with the ratchet profile 105 of the drive sleeve 100 starts to shuttle axially every time correspondingly-shaped teeth of the ratchet profiles 65, 105 mutually engage.

In this way dialing or setting of a dose is accompanied by an audible click sound as well as by the button portion 32 that eventually shuttles back and forth in an axial direction. Since the ratchet member 60 is also rotatably locked to the dose indicator 80 when the drive mechanism 8 is in dose setting mode S also the dose indicator 80 starts to rotate in a dose incrementing direction. In this way a sequence of increasing numbers shows up in the window 91 of the gauge element 90 travelling in the proximal direction. During dose setting the drive sleeve 100 is rotatably locked to the main housing 11 through the clutch C1 as illustrated in FIG. 3.

In this way, since the drive sleeve 100 is rotationally locked and since the dose indicator 80 rotates in a dose incrementing direction the last dose limiter 50 travels in an axial direction as the dose indicator 80 is rotated. In case that the amount of medicament left in the cartridge is smaller than the size of the dose to be set the last dose limiter 50 gets in abutment with a stop element on the outer surface of the drive sleeve 100, thereby preventing any further dose incrementing rotation of the dose indicator 80.

The ratchet member 60 and the dispensing member 30 are biased in proximal direction 2 by means of the spring member 70 extending axially between the abutment portion 15 and a distal end face or abutment face of the ratchet member's 60 proximal rim 61. The spring member 70 is designed to bias the ratchet member 60 towards and against the distal end face of the drive sleeve 100. This axial load acts to maintain the mutually corresponding ratchet profiles 65, 105 in engagement.

A torque required to overhaul this ratchet is governed by the axial load provided by the spring member 70, the ramp angle of the ratchet and the friction coefficient between the mating surfaces and the mean radius of the ratchet profiles 65, 105. As the user rotates the dose dial 20 in a dose incrementing direction, e.g. clockwise, the ratchet member 60 rotates relative to the drive sleeve 60 by consecutive ratchet teeth. Every time a ratchet tooth re-engages into a next detented position an audible click is generated by the mutually engaged ratchet profiles 65, 105. At the same time a tactile feedback is given to the user by the change in torque input required for rotating the dose dial 20.

For increasing a selected dose, the dose dial 20 is simply rotated further, e.g. in clockwise direction. Every time the dose is incremented by a discrete step the re-engagement of the ratchet profiles 65, 105 provides audible and tactile feedback to the user. If the user continues to increase the dose until a maximum dose limit is reached the dose indicator 80 engages with its maximum dose stop with the gauge element 90 thereby preventing any further rotation of the dose indicator 80 and hence any further rotation of the ratchet member 60, the dispensing member 30 and the dose dial 20.

Once a dose of respective size has been set or selected the user is also able to de-select or to decrement the dose. De-selecting of a dose is achieved by the user rotating the dose dial 20 in a dose decrementing direction, e.g. counter-clockwise. The torque to be applied to the dose dial 20 is sufficient to overhaul the ratchet between the ratchet member 60 and the drive sleeve 100 in the dose decrementing direction. When the ratchet is overhauled counter-clockwise also the dose indicator rotates in the opposite direction, thereby consecutively illustrating a sequence of decreasing numbers in the window 91. Also the last dose limiter 50 travels in the opposite axial direction towards its initial position.

Once a dose of required size has been set the drive mechanism 8 may be switched into a dose dispensing mode D by depressing the dispensing member 30 in distal direction 1. When the button portion 32 of the dispensing member 30 is depressed as illustrated for instance in FIG. 5, the ratchet member 60 advances in distal direction 1 against the action of the spring member 70. The ratchet engagement of the ratchet profiles 65, 105 is disengaged. In addition the clutch C3 between the ratchet member 60 and the dose indicator 80 is disengaged since the ratchet member 60 is displaced axially relative to the dose indicator 80.

Moreover and due to the axial abutment of dispensing member 30 and drive sleeve 100 also the drive sleeve 100 is displaced in distal direction 1 so that the clutch C1 between drive sleeve 100 and main housing 11 is disengaged or released. Upon axial displacement of the dispensing member 30 a radially widened shoulder portion 35 thereof axially abuts against a correspondingly-shaped shoulder portion 106 of the drive sleeve 100 thereby disengaging the detent structure 102 from the detent structure 18 of the main housing 11 as illustrated in FIG. 5. Consequently, the drive sleeve 100 is free to rotate under the action of a mainspring 126. Before the clutch C1 disengages in the course of depressing the dispensing member 30 the clutch C2 engages.

The shoulder portion 106 faces in proximal direction 2 and is located on the inside facing sidewall of the hollow drive sleeve 100. The shoulder portion 106 comprises a stepped down portion. This stepped portion is substantially even-shaped to provide reduced friction when in axial abutment with a correspondingly-shaped stepped shoulder portion 35 of the dispensing member 30. The shoulder portion 35 of the dispensing member 30 faces in the distal direction.

In dose setting mode S as shown in FIG. 3 there exists at least a small axial gap between these shoulder portions 35, 106. Consequently the axial abutment of dispensing member 30 and drive sleeve 100 is only obtained after the dispensing member 30 has been displaced a certain distance in distal direction 1 so that the ratchet engagement of ratchet member 60 and drive sleeve 100 is disengaged before the drive sleeve 100 advances in unison with the dispensing member 30 and with the ratchet member 60 in distal direction 1 to arrive in the distal dose dispensing position that defines the dose dispensing mode D.

With the distally directed displacement of the drive sleeve 100 also a clutch C2 between drive sleeve 100 and dose indicator 80 is engaged. This clutch C2 is shown in FIG. 7 in its disengaged state. Hence, the drive sleeve 100 axially extending through the hollow and sleeve-shaped dose indicator 80 comprises a toothed profile 101 to selectively engage with a correspondingly toothed profile 86 located at an inside facing sidewall section at the proximal end of the dose indicator 80. When displacing the drive sleeve 100 in distal direction 1 to arrive at the dose dispensing position the toothed profile 101 engages with the toothed profile 86 in a torque-proof way. Moreover, as shown in FIG. 7 the toothed profile 101 extends in the distal direction from a radially outwardly extending flange portion 108 of the drive sleeve 100.

During the combined distally directed displacement of dispensing member 30, ratchet member 60 and drive sleeve 100 the second clutch C2 engages before the clutch C1 disengages. Moreover, the clutch C2 also engages before the clutch C3 disengages. The clutch C1 disengages after the clutch C3 has disengaged. This is to avoid any uncontrolled rotation of the drive sleeve and to make sure that the dose actually set and dispensed exactly corresponds to the dose size as indicated by the dose indicator 80. When returning into the dose setting mode, the clutches C1, C2 and C3 engage and disengage in an inverted order.

As the clutch C2 engages the drive sleeve 100 is further in axial abutment with the proximal end of the dose indicator 80. Consequently, the dose indicator 80 axially fixed to the housing 10 also serves as a distal stop for the combined distally directed displacement of drive sleeve 100 and dispensing member 30.

During dose dispensing the drive sleeve 100 then rotates in a dose decrementing direction, e.g. counter-clockwise under the action of the mainspring 126. This rotation is equally transferred to a dose decrementing rotation of the dose indicator 80. Hence, during dose dispensing the dose indicator 80 returns into its initial position and the gauge element 90 returns into its initial position as illustrated in FIG. 1. The process of dose dispensing is terminated when the zero dose stop of the dose indicator 80 abuts with a correspondingly-shaped stop of the gauge element 90.

There are further provided mutually engaging click elements 88 and 98 on the dose indicator 80 and the gauge element 90 that audibly engage when the zero dose configuration has been reached. The click element 88 comprises a flexible arm which is to be radially outwardly biased by the axial and distal displacement of the ratchet member 60, in particular of its distal rim 62. In this way, the click element 88 of the dose indicator 80 may be radially outwardly biased by the ratchet member 60 when switched into the dose dispensing mode D. In this way, a rather loud and distinct click noise is generated directly indicating to a user, that dose dispensing has terminated.

Figure 20:
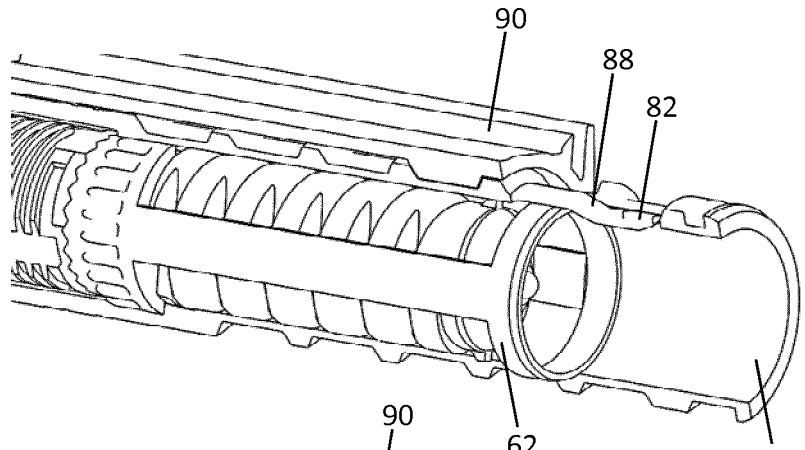
FIG. 20 is a perspective illustration of the configuration according to FIG. 16.

As it is apparent from the sequence of FIGS. 16-19 and the corresponding sequence of FIGS. 20-23 the axially aligned click element 88 integrally formed with the dose indicator 80 extends at least slightly radially inwardly into the hollow-shaped dose indicator 80. In the dose setting mode as shown in FIGS. 16 and 20 the radially inwardly extending portion of the click element 88 is located distally from the distal rim 62 of the ratchet member 60. The click element 88 extends in an axial direction and its free end 82 forms a distal end thereof. During a dose setting procedure the gauge element 90 is subject to a proximally directed displacement relative to the dose indicator 80 and hence also relative to the click element 88.

Figure 21:
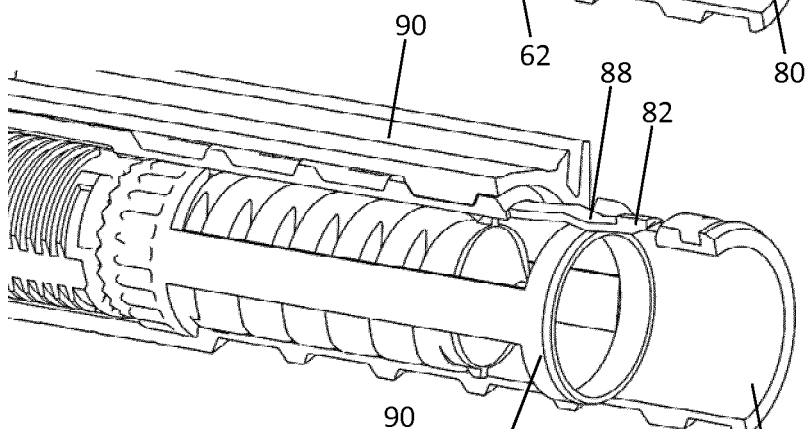
FIG. 21 is a perspective illustration of the configuration of the device according to FIG. 17.

Since the click element is in its unbiased state it is substantially disengaged from the correspondingly-shaped click element 98 of the gauge element 90 that comprises a radially outwardly extending recess in the inside facing sidewall portion of the gauge element 90. As a dose dispensing is triggered through the distally directed displacement of the dispensing member 30 and the ratchet member 60 also the distal rim 62 of the ratchet member 60 advances in distal direction 1. Then and as illustrated in FIGS. 17 and 21 the click element 88 is deflected radially outwardly.

Figure 22:
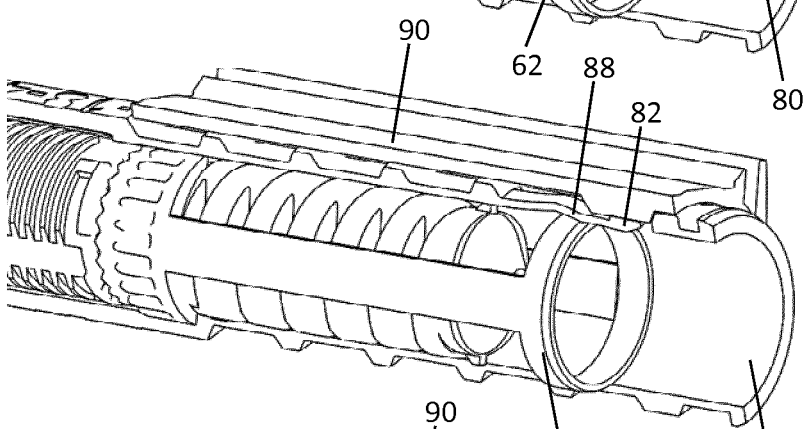
FIG. 22 is a perspective illustration of the configuration of FIG. 18
Figure 23:
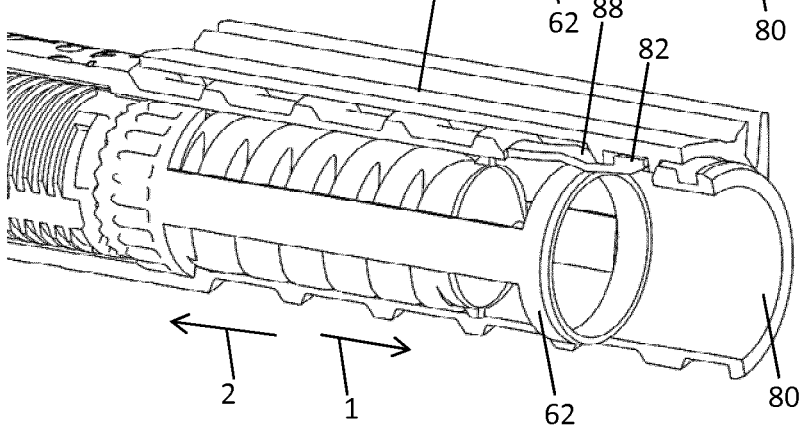
FIG. 23 is a perspective illustration of the configuration of FIG. 19.

Consequently, this radially outwardly directed displacement is largest at the free end 82 of the click element 88. It is particularly located radially outwardly compared to the outer circumference of the helical section 85 of the dose indicator 80. As shown in FIGS. 18 and 22 as the gauge element 90 returns into its initial zero dose position the click element 88, in particular its free end 82 is deflected radially inwardly. Since the click element 88 is still biased by the distal rim 62 of the ratchet member 60 radially outwardly a rather loud and distinct click noise is generated when the recessed click element 98 of the gauge element 90 engages and axially overlaps with the free end 82 of the dose indicator's 80 click element 88.

When the dispensing member 30 is released, the spring member 70 induces a proximally directed return motion to the ratchet member 60, thereby disengaging the click element 88 and the ratchet member's 60 distal rim 62. In a subsequent dose setting procedure the gauge element 90 is displaceable in the proximal direction relative to the dose indicator 80 without producing any noise.

The drive sleeve 100 is permanently rotatably engaged via the geared section 103 with the drive member 110. As already explained a rotation of the drive member 110 in dose decrementing direction leads to a distally directed displacement of the piston rod 130. In addition the drive member 110 comprises a radially outwardly protruding click element 112, indicated in FIG. 2, engaging with a correspondingly-shaped toothed profile on the interior surface of the main housing 11. In this way, delivery of a dose and hence a rotation of the drive member 110 is also accompanied by an audible click sound with each dose increment delivered.

Delivery and dispensing of a dose continues as described above while the user keeps the dispensing member 30 in a depressed position. If the user releases the dispensing member 30, the dispensing member 30 immediately returns into its initial and proximal dose setting position under the effect of the spring member 70. Consequently, also the ratchet member 60 and the drive sleeve 100 return into their dose setting positions, thereby engaging the clutches C1, C3 but releasing the clutch C2.

During dose dispensing the dose indicator 80 and the drive sleeve 100 rotate together. Since there is no relative rotation between the drive sleeve 100 and the dose indicator 80 the last dose limiter 50 remains in its axial position relative to the drive sleeve 100 and the dose indicator 80.

Once the dispensing procedure is stopped by the dose indicator 80 getting in rotational abutment with the gauge element 90 the mainspring-driven rotation of the drive sleeve 100 stops. When the user releases the dispensing member 30, in particular its button portion 32 the drive sleeve 100 will re-engage with the main housing 11 and the ratchet member 60 will re-engage with the dose indicator 80.

The mainspring 126 providing a mechanical energy storage and providing sufficient torque to expel the amount of medicament contained in the cartridge 6 comprises an elongated strip of material that has been rolled or coiled such that its natural state is to form a tightly wound spiral with a comparatively small inner diameter. One end of the elongated material strip is engaged and connected to the drive sleeve 100. The drive sleeve 100 comprises a respective coil portion 107 axially constrained by flange portions 108 as shown in FIGS. 1 and 7 that allows for a smooth and well-defined coiling of the elongated material strip of the mainspring 126.

There is further provided a storage spool 120 radially adjacent to the coil portion 107 of the drive sleeve 100. The storage spool 120 is axially intersected by the drive member 110 and is free to rotate on the outer circumference of the drive member 110. Also the storage spool comprises a distal and a proximal flange portion 122 in order to axially constrain the mainspring 126. The mainspring 126, hence the elongated strip of material, tends to coil itself onto the storage spool 120. Since one end of the mainspring 126 is anchored to the drive sleeve 100 the mainspring 126 is chargeable by rotating the drive sleeve 100 in a dose incrementing direction thereby coiling up the elongated strip of material onto the coil portion 107 of the drive sleeve 100. Once charged the majority of material of the mainspring 126 is wrapped around the drive sleeve 100. During consecutive dispense procedures the elongated strip of material transfers back to the storage spool 120 thereby inducing a number of dose decrementing rotations of the drive sleeve 100.

As shown in FIG. 3 the flange portions 108, 122 of the drive sleeve 100 and the drive member 110 are axially engaged. In this way the storage spool 120 is axially slaved or restrained by the drive sleeve 100. The storage spool 120 is axially intersected by the sleeve shaped drive member 110 and is free to slide along the drive member 110 in an axial direction. In this way, the storage spool 120 is axially displaceable in unison with the drive sleeve when switching between dose dispensing and dose setting modes, thereby keeping any axial load away from the mainspring 126.

LIST OF REFERENCE NUMERALS 1 distal direction
2 proximal direction
3 axis
3' axis
4 axis
5 injection device
6 cartridge
7 piston
8 drive mechanism
9 flange
10 housing
11 main housing
12 proximal housing portion
12a socket portion
13 protective cap
14 cartridge holder
14a threaded socket
15 abutment member
15a bearing
16 window
16a window
17 protrusion
18 detent structure
20 dose dial
21 clip member
30 dispensing member
31 shaft portion
32 button portion
34 snap member
35 shoulder portion
50 last dose limiter
60 ratchet member
61 proximal rim
62 distal rim
63 bridging portion
64 toothed profile
65 ratchet profile
70 spring member
71 distal tip
72 frangible connection
73 lobe
80 dose indicator
82 free end
84 toothed profile
85 helical section
86 toothed profile
88 click element
89 groove
90 gauge element
91 window
9/3 distal portion
95 helical section
98 click element
100 drive sleeve
100a distal end
100b proximal end
101 toothed profile
102 detent structure
103 geared section
104 threaded section
105 ratchet profile
106 shoulder portion
107 coil portion
108 flange portion
110 drive member
110' drive member
112 click element
113 geared section
113' geared section
120 storage spool
122 flange portion
126 mainspring
130 piston rod
132 bearing
133 outer thread
140 piercing assembly
141 injection needle
142 needle hub

The invention claimed is:

1. An injection device for setting and dispensing a dose of a medicament, the injection device comprising:
   a cartridge containing the medicament and comprising a piston;
   an elongate housing to accommodate the cartridge;
   a piston rod extending along a first axis and being threadedly or slidingly engaged with the housing to apply a distally directed thrust to the piston of the cartridge,
   a drive member rotationally or threadedly engaged with the piston rod and having a wheel section or geared section; and
   a drive sleeve extending along a second axis angled relative to the first axis and having a wheel section or geared section to mesh with the wheel section or geared section of the drive member,
   wherein a first radial distance between the first axis and the second axis at a distal end of the drive sleeve differs from a second radial distance between the first axis and the second axis at a proximal end of the drive sleeve,
   wherein the cartridge extends along a third axis radially offset from and parallel to the second axis and is configured to be assembled inside the housing,
   wherein the first axis and the third axis substantially overlap at a virtual crossing point and form a non-zero angle, and
   wherein the virtual crossing point is located distally from a distal end of the piston rod.

2. The injection device according to claim 1, wherein the first radial distance is larger than the second radial distance.

3. The injection device according to claim 1, wherein a difference between the first radial distance and the second radial distance is larger than 0 mm and less than 3 mm.

4. The injection device according to claim 1, wherein the non-zero angle is equal to or smaller than 3 degrees.

5. The injection device according to claim 1, wherein the wheel section or geared section of the drive sleeve is located near or at the proximal end of the drive sleeve.

6. The injection device according to claim 1, further comprising a dispensing member aligned along the second axis with a shaft portion extending through the drive sleeve and being distally displaceable against an action of a spring member to switch from a dose setting mode into a dose dispensing mode.

7. The injection device according to claim 6, wherein the spring member comprises a distal tip overlapping with the second axis and being in axial abutment with an abutment member of the housing.

8. The injection device according to claim 1, further comprising a ratchet member aligned along the second axis and having a ratchet profile at a proximal end to selectively engage with a correspondingly shaped ratchet profile at the distal end of the drive sleeve.

9. The injection device according to claim 8, further comprising a dispensing member aligned along the second axis with a shaft portion extending through the drive sleeve and being distally displaceable against an action of a spring member to switch from a dose setting mode into a dose dispensing mode,
   wherein the spring member and the ratchet member are integrally formed, and
   wherein the ratchet member is axially displaceable relative to the housing and relative to the drive sleeve against the action of the spring member to switch from the dose setting mode into the dose dispensing mode.

10. The injection device according to claim 8, further comprising a dose indicator rotationally supported on the second axis and having numbers or symbols configured to show up in a window of the housing when subject to a dose incrementing rotation or dose decrementing rotation during dose setting or dose dispensing,
    wherein the dose indicator is configured to be rotationally engaged with the ratchet member and rotationally disengaged from the drive sleeve in a dose setting mode, and
    wherein the dose indicator is configured to be rotationally engaged with the drive sleeve and rotationally disengaged from the ratchet member in a dose dispensing mode.

11. The injection device according to claim 10, wherein:
the dose indicator is axially constrained to the housing and threadedly engaged with a gauge element rotationally locked to and axially slidably supported in the housing,
the dose indicator comprises a click element extending axially and radially inside the dose indicator, and
the click element is deflectable such that a free end of the click element protrudes radially outwardly from an outer circumference of the dose indicator.

12. The injection device according to claim 11, wherein:
the ratchet member is arranged inside the dose indicator,
the ratchet member comprises a distal rim distally displaceable relative to the dose indicator for switching from the dose setting mode into the dose dispensing mode, and
the ratchet member is configured to deflect or pivot the free end of the click element radially outwardly to engage with a corresponding click element of the gauge element and produce audible or tactile feedback when reaching an end of dose configuration.

13. A drive mechanism for an injection device, the drive mechanism comprising:
a piston rod extending along a first axis and configured to apply a distally directed thrust to a piston of a cartridge;
a drive member having a wheel section or geared section, the drive member being rotationally or threadedly engaged with the piston rod such that the piston rod is axially displaced relative to the drive member to apply a distally directed thrust to a piston of a cartridge when the drive member is rotated; and
a drive sleeve extending along a second axis angled relative to the first axis and having a wheel section or geared section to mesh with the wheel section or geared section of the drive member,
wherein a first radial distance between the first axis and the second axis at a distal end of the drive sleeve differs from a second radial distance between the first axis and the second axis at a proximal end of the drive sleeve,
wherein the cartridge, which is configured to be assembled inside a housing of the injection device, extends along a third axis radially offset from and parallel to the second axis when the cartridge is disposed inside the housing,
wherein the first axis and the third axis substantially overlap at a virtual crossing point and form a non-zero angle, and
wherein the virtual crossing point is located distally from a distal end of the piston rod.

14. The drive mechanism according to claim 13, wherein the first radial distance is larger than the second radial distance.

15. A method of operating an injection device, the method comprising:
setting a dose of medicament to be dispensed by the injection device; and
dispensing the dose of medicament by causing a drive sleeve of the injection device to rotate relative to a housing of the injection device, thereby rotating a drive member of the injection device relative to the housing to distally displace a piston rod of the injection device, wherein the drive member is geared to the drive sleeve, the drive member extending along a first axis forming a non-zero angle with a second axis along which the drive sleeve extends, wherein dispensing the dose of medicament comprises depressing a dispensing member of the injection device axially engaged with a ratchet member to cause the ratchet member of the injection device to advance relative to the drive sleeve.

16. The method according to claim 15, wherein a first radial distance between the first axis and the second axis at a distal end of the drive sleeve differs from a second radial distance between the first axis and the second axis at a proximal end of the drive sleeve.

17. The method according to claim 15, wherein advancing the ratchet member relative to the drive sleeve caused by depressing of the dispensing member comprises rotationally disengaging the ratchet member from the drive sleeve and rotationally disengaging the ratchet member from a dose indicator of the injection device.

18. An injection device for setting and dispensing a dose of a medicament, the injection device comprising:
an elongate housing to accommodate a cartridge containing the medicament and comprising a piston;
a piston rod extending along a first axis and being threadedly or slidingly engaged with the housing to apply a distally directed thrust to the piston of the cartridge,
a drive member rotationally or threadedly engaged with the piston rod and having a wheel section or geared section;
a drive sleeve extending along a second axis angled relative to the first axis and having a wheel section or geared section to mesh with the wheel section or geared section of the drive member; and
a ratchet member aligned along the second axis and having a ratchet profile at a proximal end to selectively engage with a correspondingly shaped ratchet profile at a distal end of the drive sleeve,
wherein a first radial distance between the first axis and the second axis at the distal end of the drive sleeve differs from a second radial distance between the first axis and the second axis at a proximal end of the drive sleeve.

* * * * *